US010624821B2

(12) United States Patent
Renn et al.

(10) Patent No.: US 10,624,821 B2
(45) Date of Patent: Apr. 21, 2020

(54) AQUEOUS DENTAL GLASS IONOMER COMPOSITION

(71) Applicant: DENTSPLY SIRONA inc., York, PA (US)

(72) Inventors: Caroline Renn, Singen (DE); Oliver Elsner, Radolfzell (DE); Julia Gansel, Bruchsal (DE); Christian Scheufler, Engen (DE); Uwe Walz, Constance (DE); Christoph Weber, Constance (DE); Joachim E. Klee, Radolfzell (DE); Maxmilian Maier, Osnabruck (DE)

(73) Assignee: DENTSPLY SIRONA Inc., York, PA (US)

( * ) Notice: Subject to any disclaimer, the term of this patent is extended or adjusted under 35 U.S.C. 154(b) by 119 days.

(21) Appl. No.: 15/735,725

(22) PCT Filed: Jun. 13, 2016

(86) PCT No.: PCT/EP2016/063515
§ 371 (c)(1),
(2) Date: Dec. 12, 2017

(87) PCT Pub. No.: WO2016/202744
PCT Pub. Date: Dec. 22, 2016

(65) Prior Publication Data
US 2018/0353391 A1 Dec. 13, 2018

(30) Foreign Application Priority Data

Jun. 15, 2015 (EP) ..................... 15172078

(51) Int. Cl.
| | | |
|---|---|---|
| *C08F 220/18* | (2006.01) | |
| *C08F 220/60* | (2006.01) | |
| *C08F 226/02* | (2006.01) | |
| *A61K 6/083* | (2006.01) | |

(52) U.S. Cl.
CPC .......... *A61K 6/0835* (2013.01); *C08F 220/18* (2013.01); *C08F 220/60* (2013.01); *C08F 226/02* (2013.01); *C08F 2220/1825* (2013.01); *C08F 2800/10* (2013.01); *C08F 2810/50* (2013.01)

(58) Field of Classification Search
None
See application file for complete search history.

(56) References Cited

U.S. PATENT DOCUMENTS 3,655,605 A * 4/1972 Smith et al. .......... A61K 6/0023
523/116
3,814,717 A * 6/1974 Wilson et al. ....... A61K 6/0023
433/228.1
4,089,830 A * 5/1978 Tezuka ................. A61K 6/0835
106/35
4,143,018 A * 3/1979 Crisp ................... A61K 6/0675
260/998.11
4,209,434 A 6/1980 Crisp
(Continued)

FOREIGN PATENT DOCUMENTS

EP 0173567 A2 3/1986
EP 2705827 A1 3/2014
(Continued)

*Primary Examiner* — Peter A Salamon
(74) *Attorney, Agent, or Firm* — Dentsply Sirona Inc.

(57) ABSTRACT

The present invention relates to an aqueous dental glass ionomer composition comprising
(A) a reactive particulate glass,
(B) a water-soluble, polymerizable polymer comprising acidic groups, which is reactive with the particulate glass in a cement reaction, whereby the polymerizable polymer has a polymer backbone and hydrolysis-stable pendant groups having one or more polymerizable carbon-carbon double bonds, wherein the polymerizable polymer is obtainable by a process comprising
a) a step of copolymerizing a mixture comprising
(i) a first copolymerizable monomer comprising at least one optionally protected carboxylic acid group and a first polymerizable organic moiety, and
(ii) a second copolymerizable monomer comprising one or more optionally protected primary and/or secondary amino groups and a second polymerizable organic moiety,
for obtaining an amino group containing copolymer;
b) a step of coupling to the amino group containing copolymer a compound having a polymerizable moiety and a functional group reactive with an amino group of repeating units derived from the second copolymerizable monomer in the amino group containing copolymer obtained in the first step, wherein the optionally protected amino group is deprotected, so that polymerizable pendant groups are linked to the backbone by hydrolysis-stable linking groups,
and, optionally, a step of deprotecting the protected carboxylic acid group after step a) or step b), for obtaining a polymerizable polymer;
(C) a hydrolysis-stable, water-soluble monomer having one polymerizable double bond and optionally a carboxylic acid group, said monomer having a molecular weight of at most 200 Da;
(D) a polymerization initiator system; and
(E) a polymerizable hydrolysis-stable crosslinker having at least two polymerizable carbon-carbon double bonds.

14 Claims, No Drawings

(56) References Cited

U.S. PATENT DOCUMENTS

| | | | |
|---|---|---|---|
| 4,298,738 A * | 11/1981 | Lechtken | C07F 9/3252 522/38 |
| 4,317,681 A | 3/1982 | Beede | |
| 4,324,744 A * | 4/1982 | Lechtken | C07F 9/3247 522/100 |
| 4,360,605 A * | 11/1982 | Schmitt | A61K 6/0835 433/228.1 |
| 4,374,936 A | 2/1983 | Tomoika | |
| 4,376,835 A * | 3/1983 | Schmitt | A61K 6/0835 106/35 |
| 4,900,546 A * | 2/1990 | Posey-Dowty | A61L 24/001 514/29 |
| 5,130,347 A * | 7/1992 | Mitra | A61K 6/0017 433/228.1 |
| 5,154,762 A | 10/1992 | Mitra | |
| 5,501,727 A | 3/1996 | Wang | |
| 5,545,676 A | 8/1996 | Palazzotto | |
| 2002/0010227 A1* | 1/2002 | Culbertson | A61K 6/083 523/115 |
| 2004/0157954 A1* | 8/2004 | Imai | A61L 24/06 523/115 |
| 2005/0252413 A1* | 11/2005 | Kangas | A61K 6/0017 106/35 |
| 2009/0105144 A1* | 4/2009 | Vogt | A61L 24/0094 514/8.2 |
| 2009/0105367 A1* | 4/2009 | Vogt | A61L 24/001 523/116 |
| 2009/0105369 A1* | 4/2009 | Vogt | A61L 24/001 523/116 |
| 2010/0228358 A1* | 9/2010 | Leonard | A61L 24/001 623/23.62 |
| 2010/0329074 A1* | 12/2010 | Vogt | A61B 17/8825 366/190 |
| 2013/0289216 A1* | 10/2013 | Klee | A61K 6/0835 525/285 |
| 2014/0228474 A1* | 8/2014 | Qian | A61K 6/0835 523/116 |
| 2018/0353391 A1* | 12/2018 | Renn | A61K 6/0835 |

FOREIGN PATENT DOCUMENTS

| | | |
|---|---|---|
| WO | 03011232 A1 | 2/2003 |
| WO | 2012084206 A1 | 6/2012 |
| WO | 2014040729 A1 | 3/2014 |

* cited by examiner

AQUEOUS DENTAL GLASS IONOMER COMPOSITION

FIELD OF THE INVENTION

The present invention relates to an aqueous dental glass ionomer composition. Furthermore, the present invention relates to the use of a mixture comprising a specific water-soluble, polymerizable polymer comprising acidic groups and a specific water-soluble, polymerizable monomer for the preparation of a dental composition.

The aqueous dental glass ionomer composition according to the present invention provides an acid-resistant cured glass ionomer composition having excellent mechanical properties and long-term mechanical and chemical resistance.

BACKGROUND OF THE INVENTION

Dental restorative materials are known for restoring the function, morphology and integrity of dental structures damaged by physical damage or caries-related decay of enamel and/or dentin. Dental restorative materials are required to have high biocompatibility, good mechanical properties and mechanical and chemical resistance over a long period of time given the harsh conditions for a restorative material in the buccal cavity.

Dental restorative materials include glass ionomer cements having good biocompatibility and good adhesion to the dental hard tissues. Moreover, glass ionomer cements may provide cariostatic properties through the release of fluoride ions. Glass ionomer cements are cured by an acid-base reaction between a reactive glass powder and a polyalkenoic acid. However, conventional glass ionomer cements have a relatively low flexural strength and are brittle due to salt-like structures between the polyacid and the basic glass.

The mechanical properties of glass ionomer cements may be improved by the selection of the polyacidic polymer. For example, a polymer having polymerizable moieties as pendant groups can be crosslinked in order to increase the mechanical resistance of the resulting glass ionomer cement.

Japanese Patent Publication No. 2005-65902A discloses a dental adhesive composition comprising, as a polymerizable monomer containing a particular carboxylic acid, a carboxylic acid compound having a (meth)acryloyl group and a carboxyl group which are bound to an aromatic group. However, such a polymerizable monomer having an ester group quickly degrades in an acidic medium.

Chen et al. and Nesterova et al. (Chen et al., J. Appl. Polym. Sci., 109 (2008) 2802-2807; Nesterova et al., Russian Journal of Applied Chemistry, 82 (2009) 618-621) disclose copolymers of N-vinylformamide with acrylic acid and/or methacrylic acid, respectively. However, none of these documents mentions the introduction of a further polymerizable moiety into the copolymer.

WO2003/011232 discloses water-based medical and dental glass ionomer cements that can be post-polymerized after the cement reaction. The dental glass ionomer cements consist of two separate polymers, wherein one of the polymers has a pendant post-polymerizable moiety linked to the polymer through an ester bond. However, this ester bond between the polymer and the polymerizable moieties is again prone to hydrolytic cleavage in acidic media. Moreover, crosslinking of the glass ionomer may lead to the shrinkage of the dental composition in particular when the molecular weight of the crosslinking polymer is low.

WO2012/084206 A1 discloses a polymer for a dental glass ionomer cement. However, WO2012/084206 does not disclose a specific combination of components for a composition of a dental glass ionomer cement.

SUMMARY OF THE INVENTION

It is an object of the present invention to provide an aqueous dental glass ionomer composition providing improved mechanical properties including high flexural strength and a clinically relevant adhesion to tooth structure after curing, as well as hydrolysis-stability in an aqueous medium before and after curing, in particular in an acidic medium.

The present invention provides an aqueous dental glass ionomer composition comprising:
(A) a reactive particulate glass,
(B) a water-soluble, polymerizable polymer comprising acidic groups, which is reactive with the particulate glass in a cement reaction, whereby the polymerizable polymer has a polymer backbone and hydrolysis-stable pendant groups having one or more polymerizable carbon-carbon double bonds, wherein the polymerizable polymer is obtainable by a process comprising
  a) a step of copolymerizing a mixture comprising
    (i) a first copolymerizable monomer comprising at least one optionally protected carboxylic acid group and a first polymerizable organic moiety, and
    (ii) a second copolymerizable monomer comprising one or more optionally protected primary and/or secondary amino groups and a second polymerizable organic moiety,
   for obtaining an amino group containing copolymer;
  b) a step of coupling to the amino group containing copolymer a compound having a polymerizable moiety and a functional group reactive with an amino group of repeating units derived from the second copolymerizable monomer in the amino group containing copolymer obtained in the first step, wherein the optionally protected amino group is deprotected, so that polymerizable pendant groups are linked to the backbone by hydrolysis-stable linking groups, and, optionally, a step of deprotecting the protected carboxylic acid group after step a) or step b), for obtaining a polymerizable polymer;
(C) a hydrolysis-stable, water-soluble monomer having one polymerizable double bond and optionally a carboxylic acid group, said monomer having a molecular weight of at most 200 Da; and
(D) a polymerization initiator system; and
(E) a polymerizable hydrolysis-stable crosslinker having at least two polymerizable carbon-carbon double bonds.

Specifically, in the coupling step b), the polymerizable pendant groups are linked to the backbone by hydrolysis-stable linking groups. The linkage preferably does not involve an ester group.

Furthermore, the present invention provides a use of a mixture comprising: a water-soluble, polymerizable polymer comprising acidic groups, which is reactive with the particulate glass in a cement reaction, whereby the polymerizable polymer has a polymer backbone and hydrolysis-stable pendant groups having one or more polymerizable carbon-carbon double bonds, wherein the polymerizable polymer is obtainable by a process comprising a) a step of copolymerizing a mixture comprising
   (i) a first copolymerizable monomer comprising at least one optionally protected carboxylic acid group and a first polymerizable organic moiety, and
   (ii) a second copolymerizable monomer comprising one or more optionally protected primary and/or secondary amino groups and a second polymerizable organic moiety,
   for obtaining an amino group containing copolymer;
b) a step of coupling to the amino group containing copolymer a compound having a polymerizable moiety and a functional group reactive with an amino group of repeating units derived from the second copolymerizable monomer in the amino group containing copolymer obtained in the first step, wherein the optionally protected amino group is deprotected, so that polymerizable pendant groups are linked to the backbone by hydrolysis-stable linking groups,
   and, optionally, a step of deprotecting the protected carboxylic acid group after step a)
   or step b), for obtaining a polymerizable polymer; said mixture further comprising
a hydrolysis-stable, water-soluble monomer having one polymerizable double bond and optionally a carboxylic acid group, said monomer having a molecular weight of at most 200 Da, for the preparation of a dental composition. Preferably, the hydrolysis-stable, water-soluble monomer having one polymerizable double bond and optionally a carboxylic acid group includes acrylic acid.

A cured aqueous dental glass ionomer composition according to the present invention is hydrolysis-stable and has excellent mechanical properties based on the specific combination of the polymerizable polymer according to (B) and the monomer having one polymerizable double bond according to (C). After polymerization of the polymerizable polymer according to (B) and the monomer having one polymerizable double bond according to (C), the polymer may contain an increased number of acidic groups when the monomer having one polymerizable double bond according to (C) contains a carboxylic acid group. Accordingly, crosslinking by a cement reaction and adhesion to dental hard tissue may be improved.

The inventors have recognized that resin reinforced dental glass ionomer cements are subject to deterioration during storage or after curing in the mouth of the patient. The inventors have further recognized that the deterioration includes hydrolytic degradation of the resin component conventionally containing hydrolyzable moieties. The inventors have then recognized that by using a specific process for the preparation of a polymer, an improved water-soluble, hydrolysis-stable, polymerizable polymer according to (B) may be prepared at a high molecular weight which overcomes the drawbacks of conventional resin reinforced glass ionomer cements known from the prior art. In said polymerizable polymer according to (B), the introduction of amino group containing repeating units into the backbone of the polymer allows to provide high molecular weight copolymers having polymerizable pendant groups linked to the backbone by hydrolysis stable linking groups. Thereby, the disadvantages of conventional polymerizable resin components may be avoided.

The polymerizable pendant groups of the polymerizable polymer according to (B) may react with the monomer having one polymerizable double bond according to (C) whereby a graft polymer is formed. The grafted side-chains may contain additional carboxylic acid groups which can take part in a cement reaction, thereby further increasing the strength of the cured composition.

A crosslinked polymer may be obtained by a polymerizable hydrolysis-stable crosslinker having at least two polymerizable carbon-carbon double bonds which crosslinks polymerizable polymers according to (B) and grafted sidechains obtained based on monomer having one polymerizable double bond according to (C).

DETAILED DESCRIPTION OF PREFERRED EMBODIMENTS

In the following, sometimes components (A), (B), (C) and (D) of the present aqueous dental glass ionomer composition are referred to by the terms "(reactive particulate) glass according to (A)", "(water-soluble) polymerizable polymer according to (B)", "(hydrolysis-stable, water-soluble) monomer (having one polymerizable double bond) according to (C)" and "polymerization initiator system according to (D)" respectively.

The term "(co)polymerizable" as used with the terms "first copolymerizable monomer" having a "first polymerizable organic moiety", "second copolymerizable monomer" having a "second polymerizable organic moiety", "compound having a polymerizable moiety" having "polymerizable pendant groups" and the crosslinker as well as the hydrolysis-stable, water-soluble monomer having "polymerizable (carbon-carbon) double bond" respectively mean compounds capable of combining by covalent bonding in an addition polymerization to form a polymer. Said "polymerizable polymer" may be combined with a crosslinker as well as with the hydrolysis-stable, water-soluble monomer having "polymerizable (carbon-carbon) double bond" respectively to form graft polymers and/or crosslinked polymers when curing the aqueous dental glass ionomer composition.

The terms "first polymerizable organic moiety", "second polymerizable organic moiety", "polymerizable pendant groups" and "polymerizable (carbon-carbon) double bond" as used herein in connection components (B), (C) and (E) of the present aqueous dental glass ionomer composition mean any double bond capable of addition polymerization, in particular free radical polymerization, preferably a carbon-carbon double bond.

The term "curing" means the polymerization of functional oligomers and monomers, or even polymers, into a polymer network. Curing is the polymerization of unsaturated monomers or oligomers in the presence of crosslinking agents.

The term "curable" refers to a aqueous dental glass ionomer composition that will polymerize into a crosslinked polymer network when irradiated for example with actinic radiation such as ultraviolet (UV), visible, or infrared radiation, or when reacted with polymerisation initiators.

The present aqueous dental glass ionomer composition provides a cured dental glass-ionomer composition/cement. Said cured dental glass ionomer composition/cement is formed based on a reaction between (A) the reactive particulate glass, the above described components polymerizable polymer according to (B), monomer according to (C) and polymerization initiator system according to (D) in a cement reaction and a polyaddition reaction.

(A) The Reactive Particulate Glass

The term "reactive particulate glass" refers to a solid mixture of mainly metal oxides transformed by a thermal melt process into a glass and crushed by various processes, which glass is capable of reacting with a polymer containing acidic groups in a cement reaction. The glass is in particulate form Moreover, the reactive particulate glass may be surface modified, e.g. by silanation or acid treatment. Any conventional reactive dental glass may be used for the purpose of the present invention. Specific examples of particulate reactive glasses are selected from calcium alumino silicate glass, calcium alumino fluorosilicate glass, calcium aluminum-fluoroborosilicate glass, strontium aluminosilicate glass, strontium aluminofluorosilicate glass, strontium alumino-fluoroborosilicate glass. Suitable particulate reactive glasses may be in the form of metal oxides such as zinc oxide and/or magnesium oxide, and/or in the form of ion-leachable glasses, e.g., as described in U.S. Pat. Nos. 3,655,605, 3,814,717, 4,143,018, 4,209,434, 4,360,605 and 4,376,835.

Preferably, the reactive particulate glass according to (A) is a reactive particulate glass comprising:
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

The present aqueous dental glass ionomer composition preferably comprises 20 to 90 percent by weight of the reactive particulate glass, more preferably 30 to 80 percent by weight, based on the total weight of the composition.

The reactive particulate glass usually has an average particle size of from 0.005 to 100 μm, preferably of from 0.01 to 40 μm as measured, for example, by electron microscopy or by using a conventional laser diffraction particle sizing method as embodied by a MALVERN Mastersizer S or MALVERN Mastersizer 2000 apparatus.

The reactive particulate glass may have a unimodal or multimodal (e.g., bimodal) particle size distribution, wherein a multimodal reactive particulate glass represents a mixture of two or more particulate fractions having different average particle sizes.

The reactive particulate glass may be a an agglomerated reactive particulate glass which is obtainable by agglomerating a reactive particulate glass in the presence of a modified polyacid and/or polymerizable (meth)acrylate resins. The particle size of the agglomerated reactive particulate glass may be adjusted by suitable size-reduction processes such as milling.

The reactive particulate glass may be surface modified by a component according to (B), (C) and/or (D). In particular, the reactive particulate glass may be surface modified by one or more components of the polymerization initiator system (D) in order to avoid contact of the one or more components of the polymerization initiator system (D) with an acid under aqueous conditions.

The reactive particulate glass may alternatively or additionally be surface modified by a surface modifying agent. Preferably, the surface modifying agent is a silane. A silane provides a suitable hydrophobicity to the reactive particulate glass, which allows for an advantageous, homogeneous admixture with the organic components according to (B), (C) and (D) of the aqueous dental glass ionomer composition.

(B) The Water-Soluble, Polymerizable Polymer Comprising Acidic Groups

The water-soluble, polymerizable polymer comprising acidic groups is an organic polymeric compound comprising ionizable pendant groups, such as carboxylic acid groups. The carboxylic acid groups of the polymer are capable of reacting with a reactive particulate glass in a cement reaction to form a glass ionomer cement.

The water-soluble, polymerizable polymer comprising acidic groups according to (B) is obtainable by a process comprising the copolymerization step a), the coupling step b), and an optional deprotection step.

The term "polymerizable polymer" used in connection with item (B) means a polymer containing one or more polymerizable moieties capable of polymerizing and cross-linking of the polymer for improving the mechanical properties and the long-term mechanical and chemical resistance of the cured aqueous dental glass ionomer composition.

The term "water-soluble" used in connection with the term "polymerizable polymer" means that at least 0.1 g, preferably 0.5 g of the polymerizable polymer dissolves in 100 g of water at 20° C.

The water-soluble polymerizable polymer according to (B) is hydrolysis-stable, which means that the polymer is stable to hydrolysis in an acidic medium, such as in a dental composition. Specifically, the polymer does not contain groups such as ester groups which hydrolyze in aqueous media at pH 3 at room temperature within one month.

The water-soluble, polymerizable polymer comprising acidic groups according to (B) is obtainable by a process comprising step a) of copolymerizing a mixture comprising (i) a first copolymerizable monomer comprising at least one optionally protected carboxylic acid group and a first polymerizable organic moiety and (ii) a second copolymerizable monomer comprising one or more optionally protected primary and/or secondary amino groups and a second polymerizable organic moiety for obtaining an amino group containing copolymer. The mixture may also contain further monomers.

The first copolymerizable monomer to be used in step a) comprises at least one, preferably one to three, more preferably one or two, most preferably one optionally protected carboxylic acid group(s).

The protecting group of an optionally protected carboxylic acid group is not particularly limited as long as it is a carboxyl-protecting group known to those of ordinary skill in the art of organic chemistry (cf. P. G. M. Wuts and T. W. Greene, Greene's Protective Groups in Organic Synthesis, 4th Edition, John Wiley and Sons Inc., 2007). Preferably, the carboxyl-protecting group is selected from a trialkylsilyl group, an alkyl group and an arylalkyl group. More preferably, the carboxyl-protecting group is selected from an alkyl group or an arylalkyl group. Most preferably, the carboxyl-protecting group is selected from a tert-butyl group and a benzyl group. In one preferred embodiment, the carboxyl-protecting group is a tert-butyl group.

The term "polymerizable organic moiety" as used herein means an organic moiety of a molecule which can be used to covalently link this molecule in a chemical reaction (polymerization) to other molecules reactive with this moiety to form a macromolecule of repeating or alternating structural units. Preferably, this polymerizable organic moiety is a carbon-carbon double bond as in the case of an ethylenically unsaturated moiety.

In a preferred embodiment of the aqueous dental glass ionomer composition of the present invention, the first copolymerizable monomer is represented by the general formula (1):

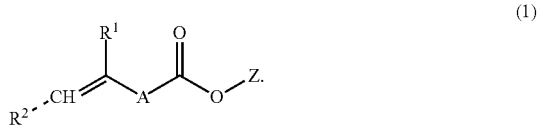

(1)

In formula (1), $R^1$ is a hydrogen atom, a —COOZ group or a straight chain or branched $C_{1-6}$ alkyl group which may be substituted by a —COOZ group. Preferably, $R^1$ is a hydrogen atom, a —COOZ group or a methyl group. More preferably, $R^1$ is a hydrogen atom or a methyl group.

In formula (1), $R^2$ is a hydrogen atom, a —COOZ group or a straight-chain or branched $C_{1-6}$ alkyl group which may be substituted by a —COOZ group. Preferably, $R^2$ is a hydrogen atom or a —COOZ group. More preferably, $R^2$ is a hydrogen atom. In formula (1), the dotted line indicates that $R^2$ may be in either the cis or trans orientation.

In formula (1), A is a single bond or a straight-chain or branched $C_{1-6}$ alkylene group which group may contain 1 to 3 heteroatoms in between two carbon atoms of the alkylene carbon chain, which heteroatoms are selected from an oxygen atom, nitrogen atom, and sulfur atom, and/or which alkylene group may contain in between two carbon atoms of the alkylene carbon chain 1 to 3 groups selected from an amide bond or a urethane bond. Preferably, A is a single bond or a straight-chain or branched $C_{1-6}$ alkylene group which group may contain a heteroatom in between two carbon atoms of the alkylene carbon chain, which heteroatom is selected from an oxygen atom or a nitrogen atom, and/or which alkylene group may contain in between two carbon atoms of the alkylene carbon chain a group selected from an amide bond or a urethane bond. More preferably, A is a single bond or a straight-chain $C_{1-6}$ alkylene group. Most preferably, A is a single bond.

In formula (1), Z which may be the same or different independently represents a hydrogen atom, a metal ion, a protecting group for a carboxylic acid group, or the Z forms with a further —COOZ group present in the molecule an intramolecular anhydride group. The metal ion may be a monovalent metal ion such as an alkali metal ion. In one embodiment, Z is a protecting group for a carboxylic acid group. In another embodiment, Z is a hydrogen atom. When Z forms with a further —COOZ group present in the molecule an intramolecular anhydride group (—C(O)OC(O)—), the further —COOZ group may be preferably present on $R^1$ such as in case of itaconic acid anhydride.

In a preferred embodiment, Z is a hydrogen atom and the polymerization reaction is conducted in an alkaline environment. In an alternative preferred embodiment, Z is a hydrogen atom and the amino groups of the first copolymerizable monomer and of the second copolymerizable monomer carry a protecting group.

Preferably, the first copolymerizable monomer is a protected (meth)acrylic acid monomer. More preferably, a first polymerizable monomer is selected from tert-butyl acrylate and benzyl acrylate. Most preferably, a first polymerizable monomer is tert-butyl acrylate.

In a preferred embodiment of the aqueous dental glass ionomer composition of the present invention, the second copolymerizable monomer is represented by the general formula (2):

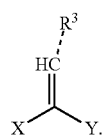

(2)

In formula (2), $R^3$ is a hydrogen atom or a straight chain or branched $C_{1-6}$ alkyl group which may be substituted by a —COOZ' group. Preferably, $R^3$ is a hydrogen atom. In formula (2), the dotted line indicates that $R^3$ may be in either the cis or trans orientation.

In formula (2), X is a protected amino group or a hydrocarbon group having 1 to 20 carbon atoms, which is substituted with an amino group which may carry a protecting group, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups. Preferably, X is a hydrocarbon group having 1 to 20 carbon atoms, which is substituted with an amino group which may carry a protecting group, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ' group. More preferably, X is a hydrocarbon group having 1 to 20 carbon atoms, even more preferably 1 to 6 carbon atoms, which is substituted with an amino group which may carry a protecting group, wherein the hydrocarbon group may contain an oxygen atom and/or which hydrocarbon group may contain an amide bond and which hydrocarbon group may further be substituted with a —COOZ' group. In as specific embodiment wherein X is a protected amino group, the compound of formula (2) is allyl amine, wherein the amino group carries a protecting group.

The protecting group of a protected amino group or an optionally protected amino group is not particularly limited and may be any conventional protecting group for an amino group as, for example, described in P. G. M. Wuts and T. W. Greene, Greene's Protective Groups in Organic Synthesis, 4th Edition, John Wiley and Sons Inc., 2007. Preferably, the amino-protecting group is selected from an acyl group, an arylalkyl group, an alkoxy carbonyl group, and an aryloxycarbonyl group. More preferably, the amino-protecting group is an acyl group. Most preferably, the amino-protecting group is a formyl group.

In formula (2), Y is a hydrogen atom or a hydrocarbon group having 1 to 20 carbon atoms, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups. Preferably, Y is a hydrogen atom or a hydrocarbon group having 1 to 20 carbon atoms, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ' group. More preferably, Y is a hydrogen atom or a hydrocarbon group having 1 to 20 carbon atoms, even more preferably 1 to 6 carbon atoms, wherein the hydrocarbon group may contain an oxygen atom and/or which hydrocarbon group may contain an amide bond and which hydrocarbon group may further be substituted with a —COOZ' group. In one preferred embodiment, Y is a hydrogen atom.

In formula (2), Z' which may be the same or different, independently represents a hydrogen atom, a metal ion, a protecting group for a carboxylic acid group, or the Z' forms with a further —COOZ' group present in the molecule an intramolecular anhydride group. In one embodiment, Z' is a protecting group for a carboxylic acid group. In another embodiment, Z' is a hydrogen atom. The metal ion may be a monovalent metal ion such as an alkali metal ion. In another embodiment, Z' is a hydrogen atom. When Z forms with a further —COOZ' group present in the molecule an intramolecular anhydride group (—C(O)OC(O)—).

In a preferred embodiment, Z' is a hydrogen atom and the polymerization reaction is conducted in an alkaline environment. In an alternative preferred embodiment, Z' is a hydrogen atom and the amino groups of the second copolymerizable monomer carry a protecting group.

In one embodiment, the second copolymerizable monomer comprises a second copolymerizable organic moiety selected from the group of (meth)acrylamide moieties which may be substituted and substituted (meth)acrylic acid which may be protected. In another embodiment, the second copolymerizable monomer is selected from allyl amine, aminopropyl vinyl ether, aminoethyl vinyl ether, N-vinyl formamide and 2-aminomethyl acrylic acid. In a preferred embodiment, the second copolymerizable monomer is aminopropyl vinyl ether. The amino group may be in the form of an ammonium salt such as a ammonium chloride. Preferred structures wherein the amino group may also carry a protecting group are depicted in Scheme 1 below.

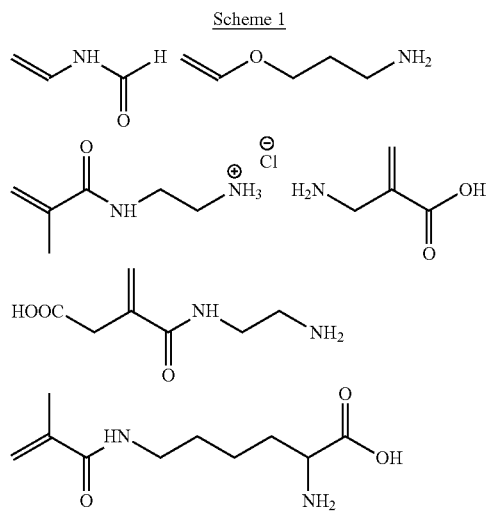

Scheme 1

The molar ratio of first copolymerizable monomer to second copolymerizable monomer in the mixture copolymerized in step a) (mol first copolymerizable monomer/mol second copolymerizable monomer) is preferably in the range of from 100:1 to 100:50, more preferably in the range from 100:2 to 100:20, still more preferably in a range from 100:3 to 100:10.

The further copolymerizable monomers optionally to be used in step a) comprise at least one, preferably one to three, more preferably one or two, most preferably one optionally protected acidic group(s) which are not carboxylic acid groups. Specific examples of acidic groups are sulfonic acid groups (—$SO_3M$), phosphonic acid groups (—$PO_3M_2$) or phosphoric acid ester groups (—$OPO_3M_2$), or salts thereof, wherein M may independently be a hydrogen atom or a monovalent ion such as an alkali metal or an ammonium ion.

Specific examples of the optional further monomers are selected from 2-acrylamido-2-methylpropane sulfonic acid, vinyl phosphonate, and vinyl sulfonic acid.

In a preferred embodiment, the solutions containing the first copolymerizable monomer and the second copolymerizable monomer are separately saturated with nitrogen before combining them for copolymerization to minimize possible side-products of a competitive Aza-Michael addition.

Step a) of the aqueous dental glass ionomer composition proceeds as a chain-growth polymerization. In one embodiment, step a) comprises radical copolymerization.

The type of copolymer formed by step a) of the present invention may be a statistical copolymer, a random copolymer, an alternating copolymer, a block copolymer or a combination thereof.

A copolymer obtained by step a) of the present invention is an amino group containing copolymer, such as, for example, a copolymer obtainable by copolymerization of acrylate and aminopropyl vinyl ether.

The reaction conditions of the polymerization reaction according to step a) of the present invention are not particularly limited. Accordingly, it is possible to carry out the reaction in the presence or absence of a solvent. A suitable solvent may be selected from the group of water, dimethyl formamide (DMF), tetrahydrofurane (THF), and dioxane.

The reaction temperature is not particularly limited. Preferably, the reaction is carried out at a temperature of between −10° C. to the boiling point of the solvent. Preferably, the reaction temperature is in the range of from 0° C. to 80° C.

The reaction time is not particularly limited. Preferably the reaction time is in the range of from 10 minutes to 48 hours, more preferably 1 hour to 36 hours.

The reaction is preferably carried out in the presence of a polymerization initiator. In a preferred embodiment of the aqueous dental glass ionomer composition, the polymerization initiator is selected from azobisisobutyronitrile (AIBN), 2,2-azobis(2-amidinopropane)dihydrochloride, 2,2'-azobis (2-methylbutyronitrile), 2,2'-azobis(N,N'-dimethyleneisobutyramidine) dihydrochloride, and 4,4'-azobis(4-cyano pentanoic acid). The amount of the polymerization initiator is not particularly limited. Suitably, the amount is in the range of from 0.001 to 5 mol % based on the total amount of the monomers.

The reaction product obtained in step a) may be isolated by precipitation and filtration, or lyophilization. The product may be purified according to conventional methods.

Step b) of the aqueous dental glass ionomer composition is a step of coupling a compound having a polymerizable moiety and a functional group reactive with an amino group of repeating units derived from the second copolymerizable monomer in the amino group containing copolymer obtained in the first step wherein the optionally protected amino group is deprotected.

Preferably, the coupling reaction in step b) is an addition reaction or a condensation reaction forming a bond selected from an amide bond, a urea bond or a thiourea bond.

The term "functional group reactive with an amino group" as used herein means any group which can form a covalent bond with an amino group of the amino group containing copolymer. Preferably, a functional group reactive with an amino group is a carboxylic acid group or a derivative thereof such as an ester group or an anhydride thereof, an isocyanate group or an isothiocyanate group. More preferably, a functional group reactive with an amino group is a carboxylic acid group or a derivative thereof.

If the amino group of repeating units derived from the second copolymerizable monomer in the amino group containing copolymer obtained in the first step is protected, the amino group can be deprotected prior to step b) or concomitant with step b).

The conditions for deprotection of an optionally protected amino group are selected according to the protecting group used. Preferably, the protected amino group is deprotected by hydrogenolysis or treatment with acid or base.

If the deprotection of a protected amino group is carried out concomitantly with step b), it will be understood by a person skilled in the art that the deprotection conditions and the conditions for step b) have to be selected so that both reactions can proceed efficiently.

In a preferred embodiment of the aqueous dental glass ionomer composition, the compound having a polymerizable moiety and a functional group reactive with an amino group of repeating units derived from the second copolymerizable monomer is a compound represented by the general formula (3):

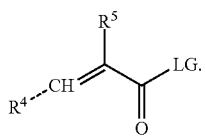

(3)

In formula (3), $R^4$ is a hydrogen atom or a straight chain or branched $C_{1-6}$ alkyl group which may be substituted by a —COOZ" group, and $R^5$ is a hydrogen atom or a straight-chain or branched $C_{1-6}$ alkyl group which may be substituted by a —COOZ" group. Preferably, $R^4$ is a hydrogen atom, and $R^5$ is a hydrogen atom or a methyl group. More preferably, $R^4$ is a hydrogen atom, and $R^5$ is a methyl group. In formula (3), the dotted line indicates that $R^4$ may be in either the cis or trans orientation.

In formula (3), Z" which may be same or different, independently represents a hydrogen atom, a metal ion, a protecting group for a carboxylic acid group, or the Z" forms with a further —COOZ" group present in the molecule an intramolecular anhydride group.

In one embodiment, Z" is a protecting group for a carboxylic acid group. In another embodiment, Z" is a hydrogen atom. In a preferred embodiment, Z" is a hydrogen atom and the polymerization reaction is conducted in an alkaline environment. In an alternative preferred embodiment, Z"s a hydrogen atom and the amino groups of the second copolymerizable monomer carry a protecting group.

In one embodiment, in formula (3), LG is a leaving group. Preferably, LG is a chlorine atom or a bromine atom, or forms with the adjacent carbonyl group a carboxylic acid anhydride moiety. More preferably, LG is a group which is suitable for reacting the compound of formula (3) in a Schotten-Baumann type reaction.

In another embodiment, LG may replace Z" and form with $R^4$ or $R^5$ an intramolecular carboxylic acid anhydride group.

In yet another embodiment two molecules of formula (3) form an intermolecular carboxylic acid anhydride group by sharing a common LG, wherein LG is an oxygen atom.

It is particularly preferred that the compound of formula (3) is acrylic acid, (meth)acrylic acid, crotonic acid, isocrotonic acid, tiglic acid, angelic acid, or an anhydride of the aforementioned acids formed of two identical or different acids; more preferably an anhydride of the aforementioned acids formed of two identical acids. Most preferably, the compound of formula (3) is (meth)acrylic anhydride.

The coupling according to step b) of the present invention serves to introduce one or more polymerizable moieties into the amino group containing copolymer, which moieties can be post-polymerized to provide additional covalent and advantageously also ionic crosslinking, imparting additional strength to the dental material.

In one embodiment of the aqueous dental glass ionomer composition, the carboxylic acid groups of the copolymer obtained in step b) are not protected and the copolymer can be used as a polymer according to the present invention without further treatment. In an alternative embodiment, the carboxylic acid groups of the copolymer obtained in step b) are protected and the carboxylic acid groups have to be deprotected before the copolymer exhibits the features of a polymer according to the present invention.

The reaction conditions of the reaction according to step b) of the present invention are not particularly limited. Accordingly, it is possible to carry out the reaction in the presence or absence of a solvent. A suitable solvent may be selected from the group of dimethyl formamide (DMF), tetrahydrofurane (THF), and dioxane.

The reaction temperature is not particularly limited. Preferably, the reaction is carried out at a temperature of between −10° C. to the boiling point of the solvent. Preferably, the reaction temperature is in the range of from 0° C. to 80° C.

The reaction time is not particularly limited. Preferably the reaction time is in the range of from 10 minutes to 48 hours, more preferably 1 hour to 36 hours.

The reaction product obtained in step b) may be isolated by precipitation and filtration. The product may be purified.

The aqueous dental glass ionomer composition optionally includes a step of deprotecting the protected carboxylic acid group after step a) or step b), for obtaining a polymerizable polymer. In a preferred embodiment, the aqueous dental glass ionomer composition includes a step of deprotecting the protected carboxylic acid group for obtaining a polymerizable polymer. In a further preferred embodiment, the aqueous dental glass ionomer composition includes a step of deprotecting the protected carboxylic acid group after step b).

The conditions for deprotection of an optionally protected carboxyl group are selected according to the protecting group used. Preferably, the protected carboxyl group is deprotected by hydrogenolysis or treatment with acid or base.

A first embodiment of the polymerizable polymer according to (B) is illustrated by the following Scheme 2, wherein a amino group protected vinyl amine is reacted with acrylic acid for obtaining a polymer backbone having a protected amino group. The copolymer is preferably a random copolymer. In a further step, the protected amino groups of the polymer backbone are liberated and coupled to a polymerizable group containing moiety, whereby a polymer of the invention is obtained having acidic groups reactive in a cement reaction wherein ionic bonds are formed, and having polymerizable groups reactive in a crosslinking reaction wherein covalent bonds are formed.

Scheme 2

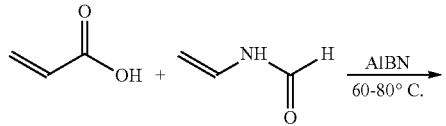

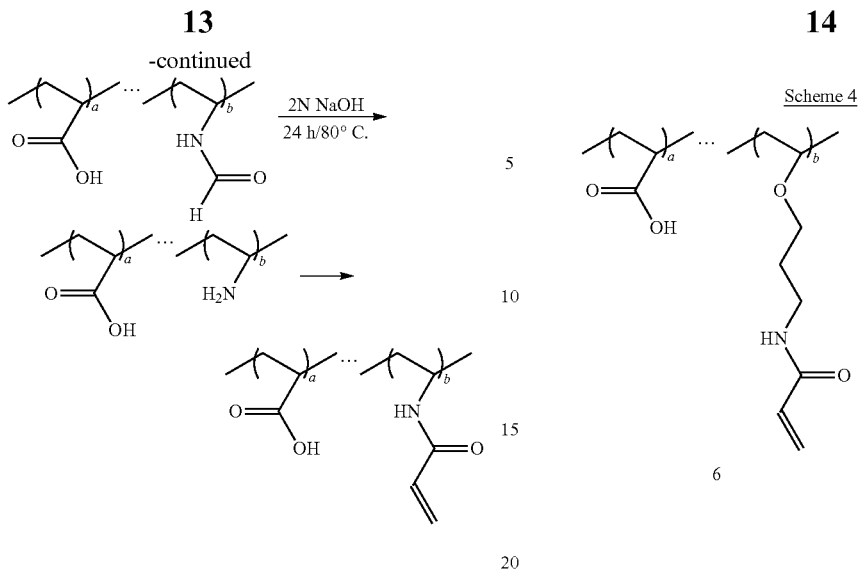

In above Scheme 2, any acrylamide group may be replaced by a methacrylamide group.

A second embodiment of the polymerizable polymer according to (B) is illustrated by the following Scheme 3, wherein protected acrylic acid is reacted with an amino group containing polymerizable vinyl ether derivative for obtaining an amino group containing polymer backbone. In a further step, the amino groups of the polymer backbone are couples to a polymerizable group containing moiety. Finally, the carboxylic acid groups are liberated whereby a polymer of the invention is obtained having acidic groups reactive in a cement reaction wherein ionic bonds are formed, and having polymerizable groups reactive in a crosslinking reaction wherein covalent bonds are formed.

Scheme 3

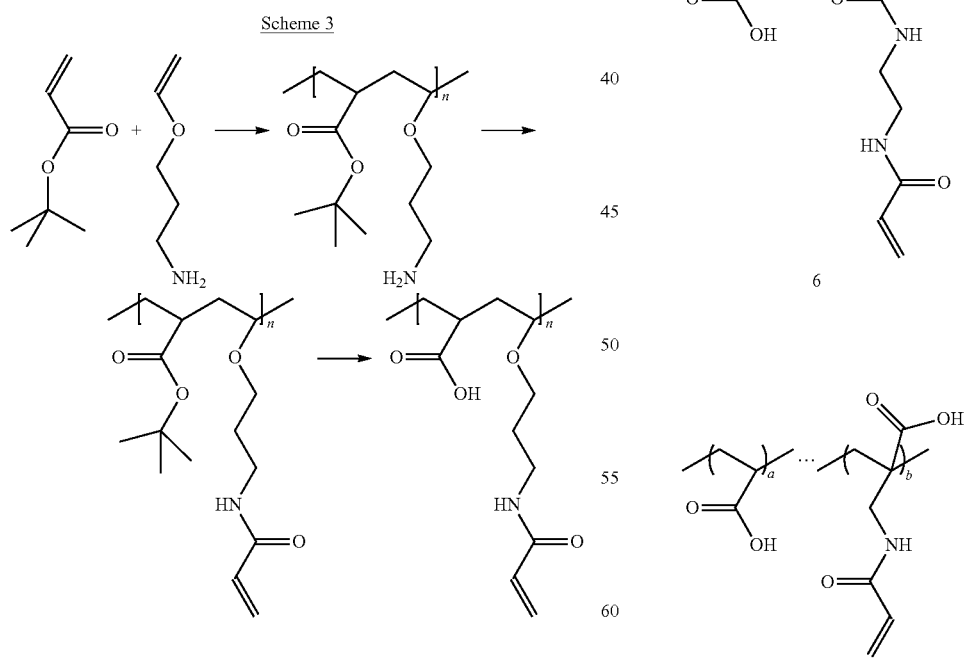

In the above Scheme 3, any acrylamide group may be replaced by a methacrylamide group The polymerizable polymer obtained in step b) may be exemplified by the following preferred structures depicted in Scheme 4 below.

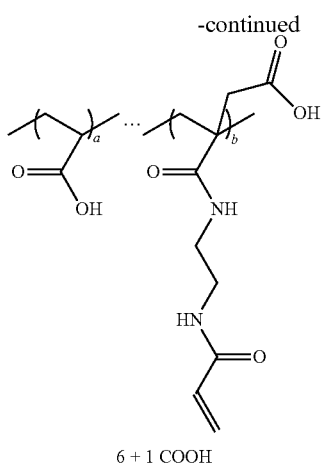

6 + 1 COOH

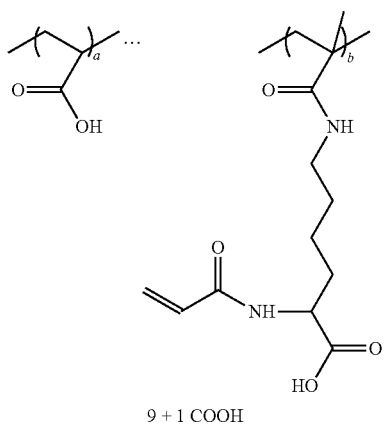

9 + 1 COOH

In the structures illustrated in Scheme 4, the numbers refer to the number of additional carbon atoms introduced by each of the side chain as compared to a corresponding polyacrylic acid. Since a polymer having (a+b) repeating units contains b times the number of additional carbon atoms in addition to the number of carbon atoms in a polyacrylic acid having (a+b) carboxylic acid groups, but b times less carboxylic acid groups, the water solubility may be reduced. On the other hand, the introduction of an additional ionic group such as a —COOH group is capable of compensating the decrease in water solubility, and is also indicated above. Preferably, the number of side chains b, the number of additional carbon atoms and the number of additional carboxylic acid groups are adjusted so as to provide a useful water solubility of the polymer of the present invention.

Accordingly, in a preferred embodiment, the side chains of the polymer which are linked to the polymer backbone via an amide bond, urea bond or thio urea bond contain one or more additional acidic groups, preferably carboxylic acid groups.

The polymerizable polymer according to (B) preferably has an average molecular weight $M_w$ in the range of from $10^3$, in particular $10^4$ to $10^6$ Da. More preferably, the average molecular weight $M_w$ is in the range of from $10^5$ to $7 \cdot 10^5$ Da, or $3 \cdot 10^4$ to $2.5 \cdot 10^5$ Da.

The polymerizable polymers according to (B) must be sufficient in number or percent by weight of carboxylic acid groups to bring about the setting or curing reaction in the presence of the reactive particulate glass according to (A) or any further unmodified or modified particulate reactive(s) and/or non-reactive filler(s). Preferably, the polymerizable polymer according to (B) is present in the aqueous dental glass ionomer composition in an amount of from 5 to 80 percent by weight, more preferably 10 to 50 percent by weight, still more preferably 15 to 40 percent by weight, based on the total weight of the composition.

(C) The Monomer Having One Polymerizable Double Bond

According to (C), the monomer having one polymerizable double bond is hydrolysis-stable and water-soluble.

The term "hydrolysis-stable" used in this connection means that the monomer according to (C) is stable to hydrolysis in an acidic medium, such as in a dental composition. In particular, the monomer according to (C) does not contain groups, e.g. as ester groups, which hydrolyze in aqueous media at pH 3 at room temperature within one month.

Further, the term "water-soluble" used in this connection means that at least 0.1 g, preferably 0.5 g of the monomer according to (C) dissolves in 100 g of water at 20° C.

The hydrolysis-stable, water-soluble monomer according to (C) is an essential component of the aqueous dental glass ionomer composition according to the invention, since the monomer according to (C) polymerizes together with the polymerizable polymer according to (B) in the presence of the polymerization initiator system according to (D). Thereby, the monomer according to (C) may polymerize with itself and/or with the polymerizable pendant groups of the polymerizable compound according to (B). Hence, besides of the formation of a polymer formed of the monomer according to (C), there is a graft polymerization wherein monomer(s) according to (C) react with the polymerizable pendant groups of the polymerizable compound according to (B), whereby a graft polymer is formed. Furthermore, the graft side chains formed of the monomer according to (C) may additionally react with the pendant polymerizable groups of another polymerizable polymer according to (B), whereby a crosslinked polymer may be obtained.

In the following Scheme 5, graft polymerisation by means of the monomer according to (C) is exemplary depicted for the polymerizable polymer according to (B) illustrated in Scheme 3 above, wherein acrylic acid is merely exemplary selected as a monomer according to (C). The letter "m" denotes an integer of at least 1.

Scheme 5

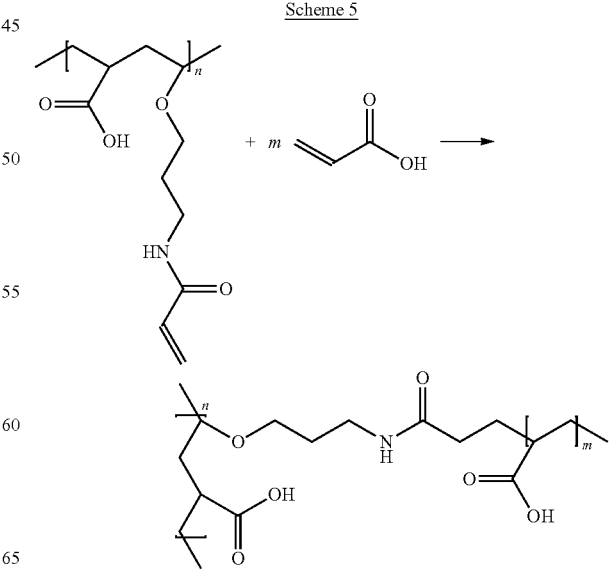

According to the present invention, one or a mixture of two or more monomers according to (C) may be used as component (C). A suitable monomer according to (C) does not contain groups hydrolysing at pH 3 within one month. In particular, a suitable monomer according to (C) does not contain any ester group.

Furthermore, a suitable monomer according to (C) contains one polymerizable double bond. Suitable polymerizable double bonds are carbon-carbon double bonds such as alkenyl groups and vinyl groups.

In a preferred embodiment of the aqueous dental glass ionomer composition, the hydrolysis-stable, water-soluble monomer having one polymerizable double bond has a carboxylic acid group and is a compound represented by the general formula (4):

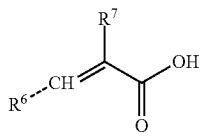

(4)

In formula (4), $R^6$ is a hydrogen atom or a straight chain or branched $C_{1-3}$ alkyl group, and $R^7$ is a hydrogen atom or a straight-chain or branched $C_{1-6}$ alkyl group which may be substituted by a —COOH group. In formula (4), the dotted line indicates that $R^6$ may be in either the cis or trans orientation. Preferably, $R^6$ is a hydrogen atom, and $R^7$ is a hydrogen atom or a $C_{1-3}$ alkyl group optionally substituted with a —COOH group. More preferably, $R^6$ is a hydrogen atom, and $R^7$ is a hydrogen atom or a methyl group substituted with a —COOH group, that is compound of formula (4) is acrylic acid or itaconic acid. Most preferably, the compound of formula (4) is acrylic acid.

In formula (4), residues $R^6$ and $R^7$ are selected with the proviso that the molecular weight of the monomer having one polymerizable double bond according to (C) is at most 200 Da, preferably at most 150 Da, more preferably at most 100 Da.

Furthermore, the hydrolysis-stable, water-soluble monomer having one polymerizable double bond may be 2-hydroxyethyl methacrylate (HEMA), hydroxypropyl methacrylate, 2-hydroxyethyl acrylamide (HEAA), N,N-dimethyl(meth)acrylamide, N,N-diethyl(meth)acrylamide, N,N-di-n-propyl(meth)acrylamide, and N-ethyl-N-methyl (meth)acrylamide.

The monomer according to (C) is preferably selected in view of a good processability and applicability of the final aqueous dental glass ionomer composition, in particular in terms of viscosity. Therefore, the viscosity of the monomer according to (C) is preferably in the range of 0.1 to 100 mPa·s, more preferably 0.3 to 50 mPa·s, even more preferably 0.5 to 25 mPa·s, yet even more preferably 0.8 to 10 mPa·s, in particular 0.9 to 3 mPa·s.

Monomers according to (C) comprising a carboxylic acid group are particularly advantageous, since such monomers introduce additional carboxylic acid groups into the acidic polymer in the aqueous dental glass ionomer composition, which can undergo a cement reaction resulting in a further improved setting or curing reaction in the presence of the reactive particulate glass according to (A).

Preferably, the monomer according to (C) is contained in the aqueous dental glass ionomer composition in an amount of from 0.1 to 20, more preferably 1 to 15 even more preferably 2 to 10 percent by weight based on the total weight of the aqueous dental glass ionomer composition. When the monomer according to (C) is absent, a long-term mechanical resistance may be low. On the other hand, when the amount monomer according to (C) exceeds 20 percent of weight, shrinkage of the dental glass ionomer cement obtained from the present aqueous dental glass ionomer composition may occur.

(D) The Polymerization Initiator System

As a polymerization initiator system according to (D), any compound or system, capable of initiating the copolymerization reaction according to the present invention may be suitably used. The polymerization initiator according to (D) may be a photoinitiator or a redox initiator or a mixture thereof.

A suitable redox initiator comprises an reducing and oxidizing agents, which typically react with or otherwise cooperate with one another to produce free-radicals capable of initiating polymerization of polymerizable double bonds in components (B) and (C) in a dark reaction, independent from the presence of light. The reducing and oxidizing agents are selected so that the polymerization initiator system is sufficiently storage-stable and free of undesirable colorization to permit storage and use under typical dental conditions. Moreover, the reducing and oxidizing agents are selected so that the polymerization initiator system is sufficiently miscible with the resin system to permit dissolution of the polymerization initiator system in the composition.

Useful reducing agents include ascorbic acid, ascorbic acid derivatives, and metal complexed ascorbic acid compounds as described in U.S. Pat. No. 5,501,727; amines, namely tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the polymerization initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

Suitable photoinitiators for polymerizing free radically photopolymerizable compositions may include binary and tertiary systems. Tertiary photoinitiators may include an iodonium salt, a photosensitizer, and an electron donor compound as described in U.S. Pat. No. 5,545,676. Suitable iodonium salts include the diaryl iodonium salts, e.g., diphenyliodonium chloride, diphenyliodonium hexafluorophosphate, diphenyl-iodonium tetrafluoroborate, and tolylcumyliodonium tetrakis(pentafluorophenyl)borate. Suitable photosensitizers are monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphorquinone, benzil, furil, 3,3,6,6-tetramethylcyclo-hexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate.

Suitable photoinitiators may also include phosphine oxides typically having a functional wavelength range of about 380 nm to about 1200 nm. Examples of phosphine oxide free radical initiators with a functional wavelength range of about 380 nm to about 450 nm include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenyl phosphine oxide, 2,3,5,6-tetramethylbenzoyldiphenylphosphine oxide, benzoyl-bis(2,6-dimethylphenyl)phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino) benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

The amount of active species of the polymerization initiator is not particularly limited. Suitably, the amount of polymerization initiator in the polymerization system according to (D) is in the range of from 0.001 to 5 mol % based on the total amount of the monomers.

(E) The Polymerizable Crosslinker Having at Least Two Polymerizable C—C Double Bonds The aqueous dental glass ionomer composition according to the present invention contains a crosslinker, which is:

(E) a polymerizable hydrolysis-stable crosslinker having at least two polymerizable carbon-carbon double bonds.

The crosslinker according to (E) may be an alkylenediol dimethylacrylate such as 1,3-butanediol dimethacrylate, 1,4-butanediol dimethacrylate, an alkylenediol divinyl ether such as 1,4-butanediol divinyl ether, di(ethylene glycol) dimethacrylate, di(ethylene glycol) divinyl ether, pentaerythritol diacrylate monostearate, ethylene glycol dimethacrylate, trimetylolpropane trimethacrylate, pentaerythritol triacrylate or triallyl ether, pentaerythritol tetraacrylate and trimetylolpropane triacrylate. The crosslinker according to (E) may also be 1,3-Bis(acrylamido)-N,N''-diethylpropane, N,N-Di(cyclopropyl acrylamido) propane.

Preferably, the crosslinker is a polymerizable compound of the following formula (5), which is disclosed in EP2705827 and WO2014040729:

$$A''\text{-}L(B)_{n'} \quad (5)$$

wherein
A'' is a group of the following formula (6)

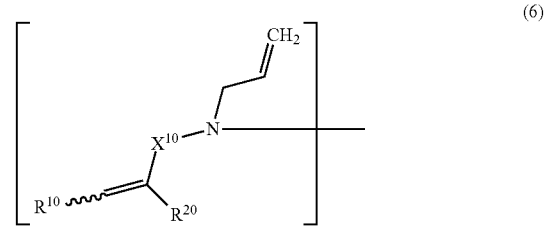

$X^{10}$ is CO, CS, $CH_2$, or a group $[X^{100}Z^{10}]_k$, wherein $X^{100}$ is an oxygen atom, a sulfur atom or NH, $Z^{10}$ is a straight chain or branched $C_{1-4}$ alkylene group, and k is an integer of from 1 to 10;

$R^{10}$ is a hydrogen atom,
—COOM$^{10}$,
a straight chain or branched $C_{1-16}$ alkyl group which may be substituted by a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$,
a $C_{3-6}$ cycloalkyl group which may be substituted by a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$,
a $C_{6-14}$ aryl or $C_{3-14}$ heteroaryl group which may be substituted by —COOM$^{10}$, —PO$_3$M$^{10}$, —O—PO$_3$M$^{10}_2$ or —SO$_3$M$^{10}$,
$R^{20}$ is a hydrogen atom,
—COOM$^{10}$
a straight chain or branched $C_{1-16}$ alkyl group which may be substituted by a $C_{6-14}$ aryl or $C_{3-14}$ heteroaryl group, —COOM$^{10}$, —PO$_3$M$^{10}$, —O—PO$_3$M$^{10}_2$ and —SO$_3$M$^{10}$,
a $C_{3-6}$ cycloalkyl group which may be substituted by a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$, or
a $C_{6-14}$ aryl or $C_{3-14}$ heteroaryl group which may be substituted by —COOM$^{10}$, —PO$_3$M$^{10}$, —O—PO$_3$M$^{10}_2$ and —SO$_3$M$^{10}$,
L is a single bond or a linker group;
B independently is
a group according to the definition of A",
a group of the following formula (7)

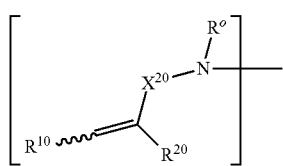

(7)

wherein
$X^{20}$ independently has the same meaning as defined for $X^1$ in formula (6),
$R^{10}$ and $R^{20}$ are independent from each other and independently have the same meaning as defined for formula (6),
$R^o$ is a hydrogen atom,
a straight chain or branched $C_{1-16}$ alkyl group which may be substituted by a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$,
a $C_{3-6}$ cycloalkyl group which may be substituted by a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$, a $C_{6-14}$ aryl group which may be substituted by —COOM$^{10}$, —PO$_3$M$^{10}$, —O—PO$_3$M$^{10}_2$ or —SO$_3$M$^{10}$,
a group of the following formula (IV)

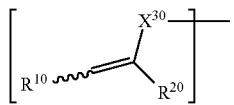

(8)

wherein
$X^{30}$ is CO, —CH$_2$CO—, CS, or —CH$_2$CS—,
$R^{10}$ and $R^{20}$ which are independent from each other and independently have the same meaning as defined for formula (6), or
a group $[X^{40}Z^{200}]_pE$,
wherein
$Z^{200}$ is a straight chain or branched $C_{1-4}$ alkylene group,
$X^{40}$ is an oxygen atom, a sulfur atom or NH,
E is a hydrogen atom,
PO$_3$M$_2$,
a straight chain or branched $C_{1-16}$ alkyl group which may be substituted by a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$, a $C_{3-6}$ cycloalkyl group which may be substituted by a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$,
a $C_{6-14}$ aryl or $C_{3-14}$ heteroaryl group which may be substituted by —COOM$^{10}$, —PO$_3$M$^{10}$, —O—PO$_3$M$^{10}_2$ or —SO$_3$M$^{10}$, and
p is an integer of from 1 to 10;
and
n' is an integer of from from 1 to 4;
wherein M$^{10}$ which are independent from each other each represent a hydrogen atom or a metal atom. Preferably, when L is a single bond, B cannot be a group according to the definition of A" or a group of the formula (7).

The following groups are preferred groups of formula (6), wherein M is a hydrogen atom or a metal atom:

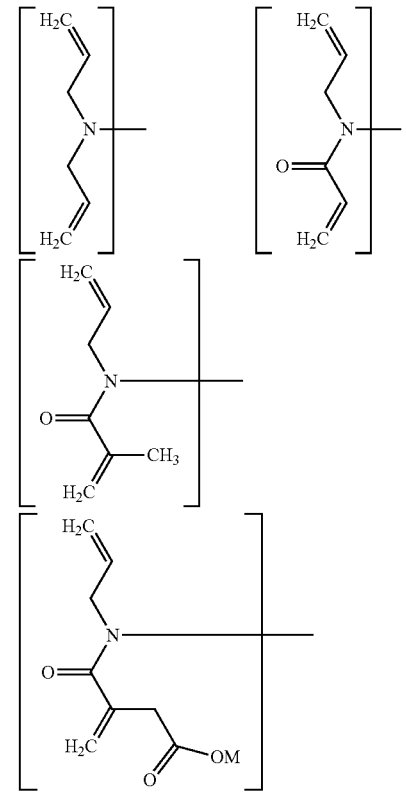

Preferred divalent linker groups may be selected from methylene, ethylene, propylene, butylene and the following divalent groups:

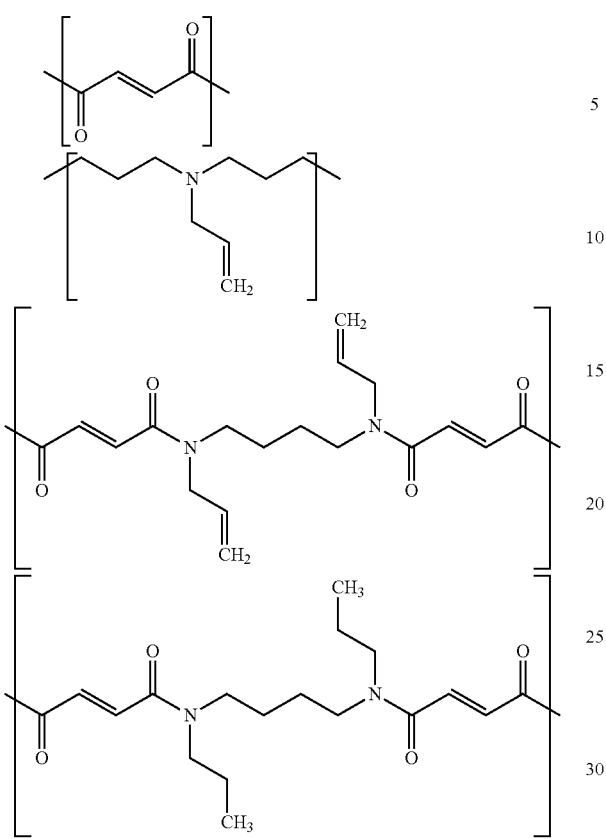

N,N'-(2E)-but-2-en-1,4-diallylbis-[(N-prop-2-en-1) amide and N,N-di(allyl acrylamido) propane are preferred.

The aqueous dental glass ionomer composition according to the present invention may contain a non-reactive filler and/or further components such as an inhibitor or a sensitizer.

The Cured Aqueous Dental Glass Ionomer Composition

The present aqueous dental glass ionomer composition is a curable dental composition, that is a cured dental glass ionomer composition/cement can be obtained therefrom by polymerizing the polymerizable polymer according to (B) and the monomer according to (C) in the presence of the reactive particulate glass (A) and the polymerization initiator system according to (D).

It was surprisingly found that when cured, the present dental glass ionomer composition has particularly advantageous mechanical properties:

Said composition's adhesive bond strength to dentin is of at least 5 MPa as measured according to ISO 29022: 2013; and said composition's flexural strength is of at least 80 MPa as measured according to ISO 4049.

Particularly Preferred Embodiments of the Aqueous Dental Glass Ionomer Composition According to a particularly preferred embodiment, the aqueous dental glass ionomer composition according to the invention comprises (A) a reactive particulate glass comprising
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride, (B) a water-soluble, polymerizable polymer comprising acidic groups, which is reactive with the particulate glass in a cement reaction, whereby the polymerizable polymer has a polymer backbone and hydrolysis-stable pendant groups having one or more polymerizable carbon-carbon double bonds, wherein the polymerizable polymer is obtainable by a process comprising a) a step of copolymerizing a mixture comprising
  (i) a first copolymerizable monomer is represented by the general formula (1'):

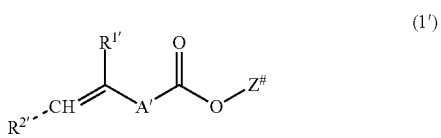

wherein $R^{1'}$ is a hydrogen atom, a —$COOZ^{\#}$ group or a methyl group;

$R^{2'}$ is a hydrogen atom or a —$COOZ^{\#}$ group;

A' is a single bond or a straight-chain or branched $C_{1-6}$ alkylene group;

$Z^{\#}$ which may be the same or different, independently represents a hydrogen atom or a protecting group for a carboxylic acid group.

(ii) a second copolymerizable monomer represented by the general formula (2'):

wherein $R^3$ is a hydrogen atom;

X' is a protected amino group or a hydrocarbon group having 1 to 6 carbon atoms, which is substituted with an amino group which may carry a protecting group, wherein the hydrocarbon group may contain a nitrogen atom;

Y' is a hydrogen atom or a hydrocarbon group having 1 to 6 carbon atoms, wherein the hydrocarbon group may contain an oxygen atom or an amide bond, and which hydrocarbon group may further be substituted with a —$COOZ^{\#\#\#}$ group;

$Z^{\#\#\#}$ which may be the same or different, independently represents a hydrogen atom or a protecting group for a carboxylic acid group, for obtaining an amino group containing copolymer;

b) a step of coupling to the amino group containing copolymer a compound having a polymerizable moiety and a functional group represented by the general formula (3'):

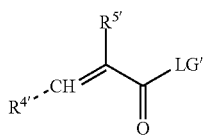

(3')

wherein
R⁴' is a hydrogen atom or a methyl group;
R⁵' is a hydrogen atom or a methyl group;
LG' is a chlorine atom or a bromine atom, or forms with the adjacent carbonyl group a carboxylic acid anhydride moiety, or wherein
two molecules of formula (3) form an intermolecular carboxylic acid anhydride group by condensation of LG', wherein LG' is an oxygen atom,
wherein the optionally protected amino group is deprotected, so that polymerizable pendant groups are linked to the backbone by hydrolysis-stable linking groups,
and, optionally, a step of deprotecting the protected carboxylic acid group after step a) or step b), for obtaining a polymerizable polymer having an average molecular weight $M_w$ in the range of from $3 \cdot 10^4$ to $2.5 \cdot 10^6$ Da;
(C) a hydrolysis-stable, water-soluble monomer having one polymerizable double bond and a carboxylic acid group, said monomer having a molecular weight of at most 200 Da is a compound represented by the general formula (4'):

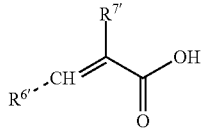

(4')

wherein
R⁶' is a hydrogen atom or a straight chain or branched $C_{1-3}$ alkyl group, and
R⁷' is a hydrogen atom or a straight-chain or branched $C_{1-3}$ alkyl group which may be substituted by a —COOH group, wherein R⁶' and R⁷' are selected with the proviso that the molecular weight of the compound of formula (4) is at most 200 Da;
preferably,
R⁶' is a hydrogen atom, and
R⁷' is a hydrogen atom or a $C_{1-3}$ group optionally substituted with a —COOH group;
more preferably,
R⁶' is a hydrogen atom, and
R⁷' is hydrogen atom or a methyl group substituted with a —COOH group;
(D) a polymerization initiator system being based on a radical initiator in the form of a photoinitiator or a redox initiator or a mixture thereof, and
(E) a polymerizable hydrolysis-stable crosslinker having at least two polymerizable carbon-carbon double bonds.
In this particularly preferred embodiment, it is preferred to select the first copolymerizable monomer represented by the general formula (1/1'), the second copolymerizable monomer represented by the general formula (2/2'), the compound having a polymerizable moiety and a functional group reactive with an amino group of repeating units derived from the second copolymerizable monomer represented by the general formula (3/3') and the hydrolysis-stable, water-soluble monomer having one polymerizable double bond represented by the general formula (4/4') as follows:

the first copolymerizable monomer:
is a protected (meth)acrylic acid monomer, more preferably tert-butyl acrylate or benzyl acrylate, most preferably tert-butyl acrylate;

the second copolymerizable monomer:
is an aminopropyl vinyl ether wherein the amino group may be in the form of an ammonium salt such as ammonium chloride, more preferably a compound selected from the following, wherein the amino group may also carry a protecting group:

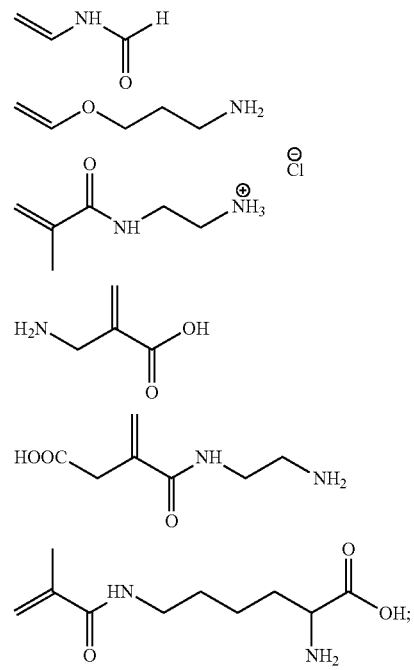

the compound having a polymerizable moiety and a functional group reactive with an amino group of repeating units derived from the second copolymerizable monomer:
is acrylic acid, (meth)acrylic acid, crotonic acid, isocrotonic acid, tiglic acid, angelic acid, or an anhydride of the aforementioned acids formed of two identical or different acids; more preferably an anyhydride of the aforementioned acids formed of two identical acids; most preferably, the anhydride of acrylic acid; and the hydrolysis-stable, water-soluble monomer having one polymerizable double bond and a carboxylic acid group:
is itaconic acid or acrylic acid, preferably acrylic acid.

In the last mentioned particularly preferred embodiment, most preferably, the polymerizable polymer obtained in step b) has one of the following structures:

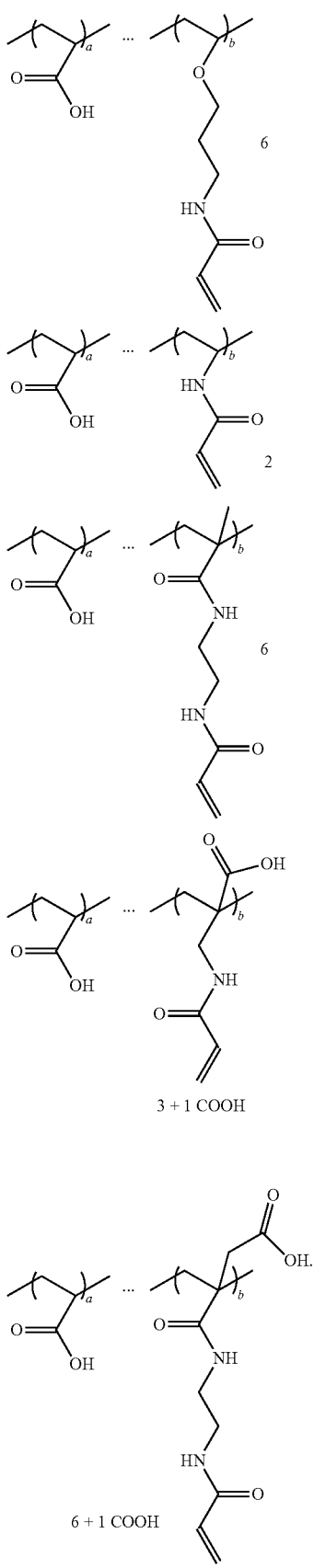

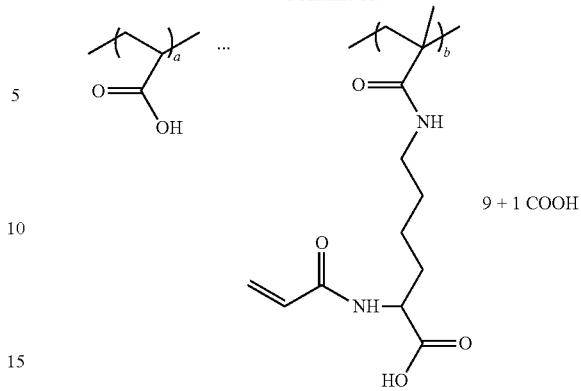

(F) The non-reactive filler

The present aqueous dental glass ionomer composition may further comprise (F) a non-reactive filler, which do not undergo a cement reaction with the polyacid polymer.

Non-reactive fillers may be included in the present aqueous dental glass composition for changing the appearance of the composition, for controlling viscosity of the composition, for further improving mechanical strength of a dental glass ionomer cement obtained from the composition, and e.g. for imparting radiopacity. The non-reactive filler should be non-toxic and suitable for use in the mouth.

The filler may be in the form of an inorganic material. It can also be a crosslinked organic material that is insoluble in the polymerizable polymer according to (B) comprised in the present aqueous dental glass ionomer composition, and is optionally filled with inorganic filler.

For example, suitable non-reactive inorganic fillers may be quartz, nitrides such as silicon nitride, colloidal silica, submicron silica such as pyrogenic silicas, colloidal zirconia, feldspar, borosilicate glass, kaolin, talc or a metallic powder comprising one or more metals or metal alloys.

Examples of suitable non-reactive organic fillers include filled or unfilled particulate polycarbonates or polyepoxides. Preferably the surface of the non-reactive organic filler particles is treated with a coupling agent in order to enhance the bond between the filler and the matrix. Suitable coupling agents include silane compounds such as gamma-methacryloxypropyltrimethoxysilane, gamma-mercaptopropyltriethoxysilane and gamma-aminopropyltrimethoxysilane.

The non-reactive filler may have a unimodal or polymodal (e.g., bimodal) particle size distribution, wherein the particulate filler preferably has an average particle size of from 0.005 to 100 μm, preferably of from 0.01 to 40 μm. The particle size may be measured, for example, by electron microscopy or by using a conventional laser diffraction particle sizing method as embodied by a MALVERN Mastersizer S or MALVERN Mastersizer 2000 apparatus. The particulate filler may be a multimodal particulate non-reactive filler representing a mixture of two or more particulate fractions having different average particle sizes. The particulate reactive filler may also be a mixture of particles of different chemical composition. The particulate non-reactive filler may be surface modified by a surface modifying agent.

Further Optional Components

The aqueous dental glass ionomer composition according to the present invention may, besides of optional component (F), comprise additional optional components.

For example, the aqueous dental glass ionomer composition according to the present invention may also include further components to improve the radio-opacity, such as CaWO$_4$, ZrO$_2$, YF$_3$ or to increase the fluoride release such as YF$_3$.

For example, the aqueous dental glass ionomer composition according to the present invention may also include a modifying agent such as tartaric acid. Such modifying agent provides for adjusting the working time and a setting time of the glass ionomer cement reaction, respectively, when preparing the cement as described in U.S. Pat. Nos. 4,089,830, 4,209,434, 4,317,681 and 4,374,936. In general, an increase in working time results in an increase in setting time as well.

The "working time" is the time between the beginning of the setting reaction when the polymer and modified particulate reactive filler are combined in the presence of water, and the time the setting reaction proceeds to the point when it is no longer practical to perform further physical work upon the system, e.g. spatulate it or reshape it, for its intended dental or medical application.

The "setting time" is the time measured from the beginning of the setting reaction in a restoration to the time sufficient hardening has occurred to allow subsequent clinical or surgical procedures to be performed on the surface of the restoration.

In a setting reaction, due to the presence of polymerizable double bonds, a polymerization reaction takes place.

The aqueous dental glass ionomer composition according to the present invention may contain further components such as solvents, pigments, nonvitreous fillers, free radical scavengers, polymerization inhibitors, reactive and nonreactive diluents e.g. bisacrylamides such as N,N'-diethyl-1, 3-bisacrylamido-propan (BADEP), 1,3-bisacrylamido-propan (BAP), and 1,3-bisacrylamido-2-ethyl-propan (BAPEN), surfactants (such as to enhance solubility of an inhibitor e.g., polyoxyethylene), coupling agents to enhance reactivity of fillers e.g., 3-(trimethoxysilyl) propyl methacrylate, and rheology modifiers.

Suitable solvents or nonreactive diluents include alcohols such as ethanol and propanol.

Suitable reactive diluents are alpha,beta unsaturated monomers for providing altered properties such as toughness, adhesion, and set time. Such alpha,beta-unsaturated monomers may be acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bisphenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates. Mixtures of alpha,beta-unsaturated monomers can be added if desired. Preferably, the mixed but unset dental compositions of the invention will contain a combined weight of about 0.5 to about 40%, more preferably about 1 to about 30%, and most preferably about 5 to 20% water, solvents, diluents and alpha,beta-unsaturated monomers, based on the total weight (including such water, solvents, diluents and alpha,beta-unsaturated monomers) of the mixed but unset aqueous dental glass ionomer composition components.

An example of a suitable free radical scavenger is 4-methoxyphenol. An example of a suitable inhibitor is tert.-butyl hydroquinone (TBHQ), hydroxytoluene or butylated hydroxytoluene (BHT). The amount of inhibitor may be selected from 0.001 to 2% and preferably from 0.02 to 0.5% based on the total weight of the polymerizable polymer according to (B)/monomer according to (C)/water mixture.

A mixture comprising the polymerizable polymer according to (B) and the monomer according to (C) may be used for the preparation of a dental composition, preferably for the preparation of a cured dental composition, more preferably for the preparation of a cured aqueous dental glass ionomer composition.

The dental composition may be a dental material to be used in the oral cavity. Dental compositions for use according to the present inventive concept represent useful restorative and filling materials, luting cements, adhesive cements, base or orthodontic cements, cavity liners and bases, pit and fissure sealants.

Preferably, the mixture comprising the polymerizable polymer according to (B) and the monomer according to (C) for use for the preparation of a dental composition in the form of an aqueous dental glass ionomer composition further comprises a reactive particulate glass according to (A) and/or a polymerization initiator system according to (D). More preferably, said mixture is an aqueous dental glass ionomer composition as defined in claim 1, wherein further preferred embodiments are set forth in subclaims 2 to 14

The invention will now be further illustrated by the following Examples.

EXAMPLES

In the following Examples 1 to 7, the preparation of preferred polymerizable polymers according to (B) is described.

Example 1

1. Copolymerisation of tert.-Butylacrylat (tButA) and 3-Aminopropylvinylether (APVE) to poly(tButA-co-APVE)

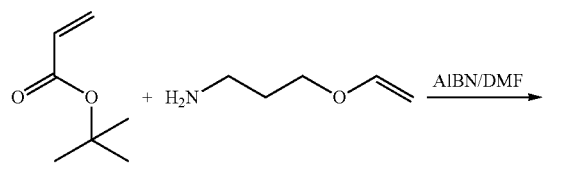

5.0 g (39 mmol) tButA, 0.99 g (9.8 mmol, 20 mol-%) APVE and 0.16 g (2 mol-%) AIBN were separately dissolved in DMF and the solutions were saturated with $N_2$. Then the solutions were combined and stirred for 24 h at 70° C. After the polymerization the cooled solution was diluted with DMF to 30 wt-% polymer solutions and precipitated in water/methanol (9:1). The separated solid was dried in vacuum.

The obtained copolymer had a molecular weight $M_n$=18 kDa, an $M_w$=51 kDa and a PD of 2.8.

IR-spectroscopy of the product showed no vinylether-vibrations while $^1$H-NMR showed broadened peaks for the aliphatic protons and no peaks for possible remaining double bond protons.

$^1$H-NMR (500 MHz, DMSO-$d_6$): δ (ppm)=3.5 (2H, 4), 2.7 (2H, 6), 2.2 (2H, 2), 1.8 (1H, 1), 1.6 (2H, 5), 1.44 (9H, 3).

2. Methacrylation of the poly(tButA-co-APVE)

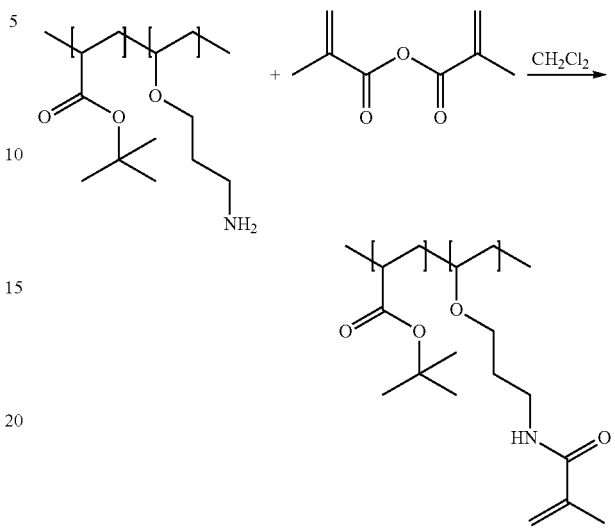

To a solution of 5 g (33.7 mmol) copolymer poly(tButA-co-APVE) dissolved in 31.5 g dichloromethane were added 1.3 g (8.42 mmol) methacrylic acid anhydride. After stirring the solution for 24 h at ambient temperature, the solvent was removed and the crude product was dissolved in 30 mL methanol. From this solution the polymer was precipitated in water, filtered off and dried in vacuum.

FT-IR: $ν_{max}$ [cm$^{-1}$]=2976, 2932, 1785, 1722 (Ester), 1670 (Amid I), 1626 (C=C), 1526 (Amid II), 1479, 1448, 1392, 1366, 1143, 844.

3. Hydrolysis of ester Moieties

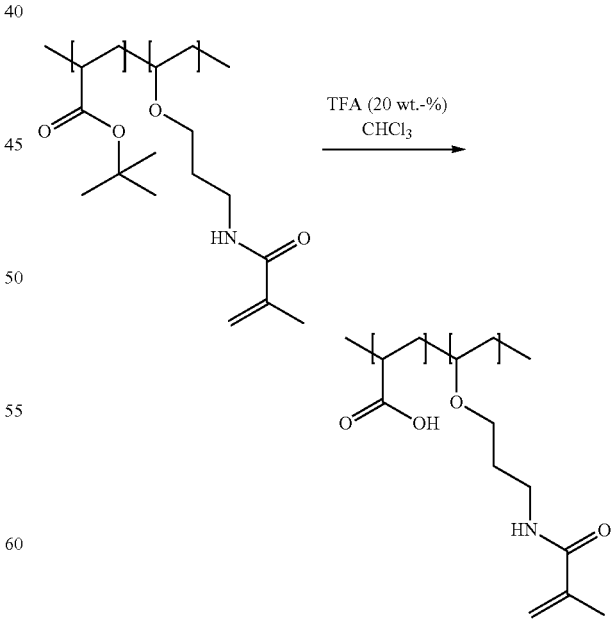

To a solution of 1.0 g (8.15 mmol) of the methacrylated poly(tButA-co-APVE) in 5 mL chloroform were added 20 wt-% trifluoro acetic acid. After stirring the solution for 5 h at 60° C. the crude precipitated polymer was separated from the solvent. The polymer was washed with chloroform, dissolved in methanol and re-precipitated in chloroform. Then the yellow polymer was dried in vacuum.

$^1$H-NMR (500 MHz, DMSO-d$_6$): δ (ppm)=12.2 (1H, —COOH), 7.8 (1H, —NH—), 5.6 (1H, —C═C—H), 5.3 (1H, C═C—H), 2.2 (2H, —CH2-backbone), 1.8 (3H, —CH$_3$), 1.8 (1H, —CH—, backbone), 1.5 (2H, O—CH$_2$CH$_2$), 1.4 (9H, C—(CH$_3$)$_3$, residual ester moieties).

Example 2

1. Copolymerization of tert butyl acrylate (t-BA) and 3-aminopropyl vinylether (APVE) to poly(AA-co-APVE)

In a three necked round bottom flask, equipped with a cooler, 2.34 mL (0.0206 mol) APVE and 8.97 mL (0.0618 mol) t-BA were mixed with 20 mL dioxane. 278 mg AIBN (2 mol-% regarding the total monomers) were dissolved, too. The reaction mixture was instantaneously flushed with Argon for about 20 min. Meanwhile a metal bath was preheated to 90° C. The polymerization was instantaneously started by placing the bath below the flask. After 1 h of stirring the reaction was complete. A sample of 5 mL was withdrawn and diluted with dioxane to 20 mL. The polymer was precipitated by adding this solution to an excess of 150 mL water. The polymer was dried at the vacuum pump. The molecular weight was determined by using SEC with DMF as eluent.

$M_n$=11500 g/mol, $M_w$=38100 g/mol, PD=3.32

2. Modification of poly(AA-Co-APVE) with methacrylic anhydride

To the residue of the reaction mixture from synthetic step 1 cooled down to room temperature were added 26 mg tert.-butyl hydroquinone (TBHQ) to deactivate the residual initiator. Than 0.0309 mol methacrylic anhydride were added. After stirring the mixture for 2 h at room temperature, the solvent was removed at the rotary evaporator (30° C.) and afterwards the sample was dried at the vacuum pump. The NMR-spectra shows broadened peaks at 5.30 ppm and 5.64 ppm of double bonds indicating that the modification was successful.

3. Hydrolysis of tert.-butyl ester Moieties 20 g of a polymer with 5 mol-% APVE incorporated were modified with methacrylic anhydride as described above. After removing the solvents at the rotary evaporator the crude product was dissolved in 50 mL of trifluoroacetic acid. The mixture was cooled in an ice bath which was slowly dissolving and stirred for 24 h. Over night the polymer precipitated. The suspension was decanted and the polymer was dissolved in 100 mL of dioxane. It was precipitated in a fivefold excess of acetone. The precipitate was dissolved again in dioxane and precipitated again. Afterwards the polymer was first dried at the rotary evaporator and afterwards at the vacuum pump. The NMR-spectra shows that the peak of the tert-butyl group at 1.38 ppm has nearly vanished. This corresponds to a degree of hydrolysis of 98 mol-%.

Example 3

Copolymerisation of tert.-Butylacrylate and 3-Aminopropylvinylether —P(tBu-co-APVE)

A solution of 15 g (117 mmol) tert.-Butylacrylat in 38 g DMF was saturated under ice cooling with nitrogen. 3 g (29 mmol) 3-Amino-propylvinylether were added to this solution after 15 minutes. Further 5 minutes later were added 480 mg (2 mol-%) AIBN in nitrogen counter flow. Then the solution was stirred for 24 h at 70° C. After the polymerization the cooled solution was diluted with DMF to 33 wt-% polymer solutions and precipitated in the 20-fold quantity of water. The solid was filtered off, washed with water and dried in vacuum.

FT-IR: $v_{max}$ [cm$^{-1}$]=2977 (—CH$_2$—), 1723 (ester), 1481, 1449, 1392, 1366, 1255, 1144, 845.

$^1$H-NMR (500 MHz, CDCl$_3$): δ (ppm)=3.5 (2H, —O—CH$_2$—), 2.7 (2H, —CH$_2$—NH$_2$), 2.2 (2H, backbone), 1.8 (1H, backbone), 1.6 (2H, —O—CH$_2$—CH$_2$—), 1.44 (9H, -tbutyl).

GPC (DMF): $M_n$=26 kDa, $M_w$=70 kDa, $M_z$=124 kDa, PD=2.7.

The following table shows typical molecular masses for different polymerization samples using a ratio of eq(tBA): eq(APVE)=3:1:

| Batch # | c(AIBN) [mol-%] | $t_{term.}$ [min.] | $M_n$ | $M_w$ | $M_z$ | PD |
|---|---|---|---|---|---|---|
| 044-020 | 4 | 10 | 35.600 | 81.000 | 137.000 | 2.3 |
| | | 30 | 40.000 | 64.200 | 94.000 | 1.6 |
| | | 60 | 40.400 | 60.700 | 85.100 | 1.5 |
| | | 1440 | 36.000 | 65.200 | 97.300 | 1.8 |
| 044-022 | 1 | 10 | 14.900 | 37.400 | 72.900 | 1.9 |
| | | 30 | 14.800 | 39.200 | 71.700 | 1.8 |
| | | 60 | 150.800 | 160.200 | 166.400 | 1.0 |
| 044-023 | 0, 1 | 30 | 69.700 | 106.900 | 146.400 | 1.5 |

Itaconic Amide Modified P(tBA-co-APVE-IA)

To a clear solution of 3.0 g p(tBA-co-APVE) in 10 mL dichloro methane were added portion wise under stirring 0.4 g (3.6 mmol) itaconic acid anhydride, whereby the solution discolorates red and then yellowish. Then the solution was stirred for 24 h at room temperature prior to evaporate dichloro methane.

FT-IR: $v_{max}$ [cm$^{-1}$]=2977 (—CH$_2$—), 1718 (ester), 1668 (amide I), 1559 (amide II), 1476, 1437, 1392, 1367, 1252, 1146, 1100, 945, 843.

Hydrolysis of Ester Moieties to P(AA-co-APVE-IA)

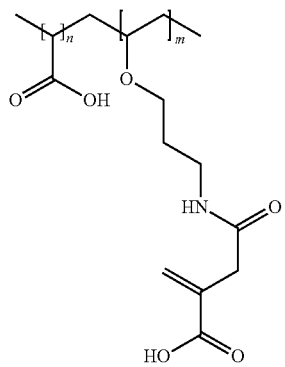

The modified polymer was added portionwise under stirring to 10 mL trifluoroacetic acid, and stirred some hours at room temperature prior to evaporate the trifluoroacetic acid in vacuum. The obtained high viscous polymer was dissolved in water and dialyzed for 4 days (MWCO=1000 g/mol). After frieze drying a reddish solid was received.

FT-IR: $v_{max}$ [cm$^{-1}$]=3392, 2932 (—CH$_2$—), 1699 (acid), 1625 (—C═C), 1546 (amide II), 1447, 1407, 1230, 1164, 1094, 934, 798, 610

$^1$H-NMR (300 MHz, D$_2$O): δ (ppm)=8.0 (1H, —NH—), 6.4 (1H, —C=C—H), 5.6 (1H, —C=C—H), 3.5 (2H, —O—CH$_2$—), 3.4 (2H, —NH—CH$_2$—), 3.3 (2H, —NH—CO—CH$_2$), 2.4 (1H, backbone), 2.0-1.5 (2H, backbone), 1.6 (2H, —O—CH$_2$—CH$_2$—).

Example 4

Methacrylamide Modified P(tBA-co-APVE-MA)

To a clear solution of 3.0 g p(tBA-co-APVE) of example 2 dissolved in 10 mL dichloromethane, 0.6 g (4.1 mmol) methacrylic acid anhydride was added dropwise. Then the solution was stirred for 24 h at room temperature prior to evaporation of dichloromethane. The obtained raw product was applied for further reactions without purification.

FT-IR: ν$_{max}$ [cm$^{-1}$]=3351, 2977 (—CH$_2$—), 1721 (ester), 1668 (amide I), 1622 (—C=C), 1531 (amide II), 1452, 1392, 1366, 1255, 1146, 1089, 940, 845.

Hydrolysis of Ester Moieties to P(AA-co-APVE-MA)

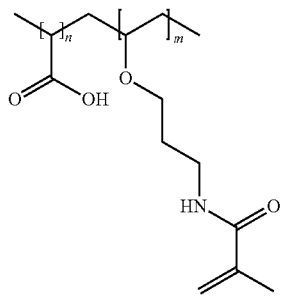

The modified polymer was added portion wise under stirring to 10 mL trifluoro acetic acid, and stirred some hours at room temperature prior to evaporate the trifluoro acetic acid in vacuum. The obtained high viscous polymer was dissolved in water and dialyzed for 4 days (MWCO=1000 g/mol). After frieze drying a colorless solid was received.

FT-IR: ν$_{max}$ [cm$^{-1}$]=3180, 2934 (—CH$_2$—), 2613, 1701 (acid), 1650 (amide I), 1597, 1537 (amide II), 1449, 1408, 1211, 1162, 1110, 919, 797, 611

$^1$H-NMR (300 MHz, D$_2$O): δ (ppm)=8.0 (1H, —NH—), 5.7 (1H, —C=C—H), 5.4 (1H, —C=C—H), 3.5 (2H, —O—CH$_2$—), 3.5 (2H, —NH—CH$_2$—), 2.2 (1H, backbone), 1.8-1.6 (2H, backbone), 1.6 (2H, —O—CH$_2$—CH$_2$—).

Example 5

Acrylamide Modified P(tBA-co-APVE-AA)

To a solution of 5.0 g p(tBA-co-APVE) of example 4 dissolved in 30 mL THF were added under ice cooling drop wise 0.76 g (6.7 mmol) acryloyl chloride, whereby immediately a white solid precipitates. The reaction mixture was stirred for further 24 h at room temperature. The solid was filtered off and the solvent was evaporated. The crude raw material was used for hydrolysis without further purification.

FT-IR: ν$_{max}$ [cm$^{-1}$]=3289, 2976 (—CH$_2$—), 1722 (ester), 1659 (amide I), 1628 (—C=C), 1544 (amide II), 1480, 1448, 1366, 1254, 1143, 844.

Hydrolysis of Ester Moieties to P(AA-co-APVE-AA)

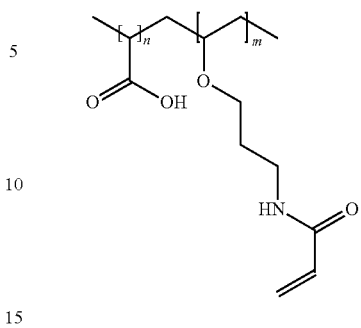

3 g of the modified polymer was added portion wise under stirring to 10 mL trifluoro acetic acid, and stirred some hours at room temperature prior to evaporate the trifluoro acetic acid in vacuum. The obtained high viscous polymer was dissolved in water and adjusted to pH 2 by addition of aqueous NaOH. Then the solution was dialyzed for 4 days (MWCO=1000 g/mol). After frieze drying a colorless solid was received.

FT-IR: ν$_{max}$ [cm$^{-1}$]=3361, 2930 (—CH$_2$—), 1707 (acid), 1654 (amide I), 1620 (—C=C), 1544 (amide II), 1447, 1407, 1242, 1179, 1097, 980, 801.

$^1$H-NMR (300 MHz, D$_2$O): δ (ppm)=6.3 (1H, —C=C—H), 6.2 (1H, —C=C—H), 5.8 (1H, —CH=C<), 3.6 (2H, —O—CH$_2$—), 3.3 (2H, —NH—CH$_2$—), 2.2 (1H, backbone), 1.9-1.4 (2H, backbone), 1.6 (2H, —O—CH$_2$—CH$_2$—).

Example 6

Copolymerisation of Acrylic Acid and N-vinyl Formamide[1] to P(AA-NVFA)

[1] N. A. Nesterova et alter, *Russian Journal of Applied Chemistry* 2008, Vol. 82, No. 4, pp. 618-621

3 g (41.6 mmol) acrylic acid and 590 mg (8.9 mmol) N-Vinylformamide were dissolved in 10.88 g distilled isopropanol and aerated with nitrogen for 30 minutes. Then 164 mg (2 mol-%) AIBN were added in the nitrogen counter flow and aerated with nitrogen for further 15 minutes. Then the solution was stirred for 24 h at 70° C., whereby a colorless solid precipitated. The solid was filtered off and washed repeatedly with acetone and dried under reduced vacuum. One obtained a colorless, fine dispersed solid.

FT-IR: ν$_{max}$ [cm$^{-1}$]=3272 (—NH$_2$), 3054 (—CH$_2$—), 2922, 1708 (acid), 1643 (amide I), 1532 (amide II), 1444, 1385 (—CH$_2$—), 1244, 1178.

$^1$H-NMR (300 MHz, DMSO-d$_6$): δ (ppm)=12.2 (1H, —COOH), 7.9 (1H, —NH—COH), 4.3 (1H, —CH—NH), 2.2 (1H, —CH—COOH), 1.7 (2H, —CH$_2$—CH—NH—), 1.5 (2H, CH$_2$—CHCOOH).

GPC (H$_2$O): M$_n$=10 kDa, M$_w$=49 kDa, M$_z$=126 kDa, PD=5.0.

Conversion of P(AA-co-NVFA) into P(AA-co-VAm) (based on the hydrolysis of pure p(VFA) to provide p(VAm), in K. Yamamoto et alter, *Journal of Applied Polymer Science* 2002, Vol. 89, pp. 1277-1283.

200 mg of the copolymer p(AA-co-NVFA) were dissolved in 10 mL 2 N NaOH and stirred for 2 h at 100° C. Then the solution was neutralized by HCl and dialyzed for 3 days (MWCO=1000 g/mol). After freeze drying a fleece-like colorless solid was obtained.

FT-IR: □$_{max}$ [cm$^{-1}$]=3274 (—NH$_2$), 2919 (—CH2-), 1666 (—COONa), 1559 (—NH$_2$), 1448, 1408 (—CH$_2$—), 1188 (—C—O—).

¹H-NMR (300 MHz, D₂O): δ (ppm)=2.5 (1H, —CH—NH₂), 2.0 (1H, —CH—COOH), 1.4 (2H, —CH₂—CH—NH₂), 1.3 (2H, —CH₂—CH—COOH).

Acrylamide Modified P(AA-co-VAm-MA)

0.5 g of the hydrolyzed copolymer P(AA-co-VAm) were added to a round bottom flask and an excess of 1.0 g methacrylic anhydride were added. The mixture was heated to 60° C. for 4 hours. Then the product was diluted in water and the polymer was precipitated in methanol twice. The final polymer was analyzed for functionalization with double bonds by ¹H-NMR (C=C bonds at 5.51 ppm and 5.31 ppm). The polymer is soluble in water after stirring for 24 hours. The degree of functionalization reaches 4.0 mol-%.

Example 7

Copolymerisation of acrylic acid and N-(2-amino ethyl)methacryl amide hydrochloride 0.2 g (3 mmol) acrylic acid and 0.5 g (3 mmol) N-(2-amino ethyl)methacryl amide hydrochloride were dissolved in 1.4 g DMF and aerated with nitrogen for 15 minutes. Then 20 mg (2 mol-%) VA-044 were added in the nitrogen counter flow and aerated with nitrogen for further 5 minutes. Then the solution was stirred for 2 h at 70° C., whereby a colorless solid precipitates. The solid was filtered off and washed repeatedly with acetone and dried under reduced vacuum. One obtained a colorless, fine dispersed solid.

FT-IR: ν$_{max}$ [cm⁻¹]=3350 (—NH₂), 2926, 1705 (acid), 1629 (amide I), 1527 (amide II), 1482, 1456, 1393, 1365, 1232, 1166, 837.

¹H-NMR (300 MHz, DMSO-d₆): δ (ppm)=12.3 (1H, —OH), 8.3 (1H, —NH—), 7.9 (2H, —NH₂), 4.2 (1H, CH3-CH<), 2.9 (2H, —NH—CH₂—), 2.6 (2H, —NH—CH₂—CH₂—), 1.5 (1H, backbone), 1.2 (3H, —CH₃), 1.0 (2H, backbone).

Example 7

The composition of the liquids 1 to 11 and of comparison liquids A, B and C are summarized in Table 1. For preparing the resin modified glass ionomer (RMGI) test specimens, the liquid was always mixed with silanated reactive glass in the form of fluoro-aluminium-silicate glass in a powder/liquid ratio of 2.8/1. The resulting mixture was filled in a transparent mold and cured for 20 s at each site with LicuLite® (from Dentsply DeTrey GmbH, Germany).

The flexural strength of the glass ionomer composition based on liquids of example 1 to 11 and of comparison example 1 and 2 are given in Table 1. The flexural strength was tested according to ISO 4049, with the only difference that the specimens were stored after irradiation for 1 h in 100% humidity at 37° C., and thereafter for 23 h in water at 37° C.

TABLE 1

Composition of the liquids 1 to 11 and of comparison liquids A and B and flexural strength of the glass ionomer compositions

| Liquid | modified PAA wt % | unmodified PAA wt % | BADEP wt % | BAABE wt % | DAAP wt % | DCP-BAP wt % | AA wt % | DEAA wt % |
|---|---|---|---|---|---|---|---|---|
| 1  | 33.0 | 0.0  | 17.4 | 0.0  | 0.0  | 0.0  | 6.6  | 12.0 |
| 2  | 35.0 | 0.0  | 14.5 | 0.0  | 0.0  | 0.0  | 7.8  | 0.0  |
| 3  | 35.0 | 0.0  | 12.0 | 0.0  | 0.0  | 0.0  | 1.3  | 12.7 |
| 4  | 35.0 | 0.0  | 16.4 | 0.0  | 0.0  | 0.0  | 0.6  | 13.0 |
| 5  | 35.0 | 0.0  | 12.0 | 0.0  | 0.0  | 0.0  | 7.7  | 3.2  |
| 6  | 35.0 | 0.0  | 18.0 | 0.0  | 0.0  | 0.0  | 3.5  | 4.2  |
| 7  | 35.0 | 0.0  | 12.0 | 0.0  | 0.0  | 0.0  | 0.0  | 18.0 |
| 8  | 35.0 | 0.0  | 12.3 | 0.0  | 0.0  | 0.0  | 0.0  | 9.1  |
| 9  | 35.0 | 0.0  | 0.0  | 15.0 | 0.0  | 0.0  | 15.0 | 0.0  |
| 10 | 35.0 | 0.0  | 0.0  | 0.0  | 15.0 | 0.0  | 15.0 | 0.0  |
| 11 | 35.0 | 0.0  | 0.0  | 0.0  | 0.0  | 15.0 | 15.0 | 0.0  |
| A  | 0.0  | 35.0 | 15.0 | 0.0  | 0.0  | 0.0  | 15.0 | 0.0  |
| B  | 43.1 | 0.0  | 17.3 | 0.0  | 0.0  | 0.0  | 0.0  | 0.0  |
| C  | 35.0 | 0.0  | 0.0  | 0.0  | 0.0  | 0.0  | 0.0  | 0.0  |
| D  | 43.2 | 0.0  | 0.0  | 0.0  | 0.0  | 0.0  | 17.2 | 0.0  |

| Liquid | HEAA wt % | MAA wt % | maleic acid wt % | water wt % | Initiator/Inhibitor wt % | total | Example | Flexural strength MPa |
|---|---|---|---|---|---|---|---|---|
| 1  | 0.0 | 0.0 | 0.0 | 30.7 | 0.3 | 100.0 | 1 | 91.8 |
| 2  | 7.7 | 0.0 | 0.0 | 33.7 | 1.3 | 100.0 | 2 | 90.1 |
| 3  | 4.0 | 0.0 | 0.0 | 33.8 | 1.1 | 100.0 | 3 | 83.7 |
| 4  | 0.0 | 0.0 | 0.0 | 33.7 | 1.3 | 100.0 | 4 | 86.9 |
| 5  | 3.4 | 3.7 | 0.0 | 33.7 | 1.3 | 100.0 | 5 | 93.7 |
| 6  | 0.0 | 1.6 | 2.6 | 33.8 | 1.2 | 100.0 | 6 | 81.2 |
| 7  | 0.0 | 0.0 | 0.0 | 33.9 | 1.1 | 100.0 | 7 | 88.5 |
| 8  | 0.0 | 8.6 | 0.0 | 33.8 | 1.3 | 100.0 | 8 | 81.6 |
| 9  | 0.0 | 0.0 | 0.0 | 33.9 | 1.1 | 100.0 | 9 | 96.0 |
| 10 | 0.0 | 0.0 | 0.0 | 33.9 | 1.1 | 100.0 | 10 | 83.5 |
| 11 | 0.0 | 0.0 | 0.0 | 33.9 | 1.1 | 100.0 | 11 | 95.9 |
| A  | 0.0 | 0.0 | 0.0 | 33.8 | 1.2 | 100.0 | Comparative example 1 | 83.4 |
| B  | 0.0 | 0.0 | 0.0 | 38.4 | 1.2 | 100.0 | Comparative example 2 | 64.6 |

TABLE 1-continued

Composition of the liquids 1 to 11 and of comparison liquids A and B and flexural strength of the glass ionomer compositions

| C | 0.0 | 0.0 | 0.0 | 63.8 | 1.2 | 100.0 | Comparative example 3 | 21.0 |
|---|---|---|---|---|---|---|---|---|
| D | 0.0 | 0.0 | 0.0 | 38.4 | 1.2 | 100.0 | Comparative example 4 | 37.7 |

| | |
|---|---|
| modified PAA | methacrylated poly-(acrylic acid-co-3-aminopropylvinylether) (p(AA-co-APVE-AA); MOPOS) |
| unmodified PAA | poly(acrylic acid-co-itaconic acid) (p(AA-co-IA)) |
| BADEP | 1,3-Bis(acrylamido)-N,N'-diethylpropane |
| BAABE | N,N'-(2E)-but-2-en-1,4-diallylbis-[(N-prop-2-en-1) amide |
| DAAP | N,N-Di(allyl acrylamido) propane |
| DCP-BAP | N,N-Di(cyclopropyl acrylamido) propane |
| AA | Acrylic acid |
| DEAA | Diethylacrylamide |
| HEAA | Hydroxyethylacryl amide |
| MAA | Methacrylic acid |
| CQ | Camphorquinone — initiator |
| DMABN | Dimethylamino benzonitril — initiator |
| TBHQ | tert.-Butylhydroquinone — inhibitor |

The invention claimed is:

1. An aqueous dental glass ionomer composition comprising (A) a reactive particulate glass, (B) a water-soluble, polymerizable polymer comprising acidic groups, which is reactive with the particulate glass in a cement reaction, whereby the polymerizable polymer has a polymer backbone and hydrolysis-stable pendant groups having one or more polymerizable carbon-carbon double bonds, wherein the polymerizable polymer is obtainable by a process comprising a) a step of copolymerizing a mixture comprising (i) a first copolymerizable monomer comprising at least one optionally protected carboxylic acid group and a first polymerizable organic moiety, and (ii) a second copolymerizable monomer comprising one or more optionally protected primary and/or secondary amino groups and a second polymerizable organic moiety, for obtaining an amino group containing copolymer;

b) a step of coupling to the amino group containing copolymer a compound having a polymerizable moiety and a functional group reactive with an amino group of repeating units derived from the second copolymerizable monomer in the amino group containing copolymer obtained in the first step, wherein the optionally protected amino group is deprotected, so that polymerizable pendant groups are linked to the backbone by hydrolysis-stable linking groups, and, optionally, a step of deprotecting the protected carboxylic acid group after step a) or step b), for obtaining a polymerizable polymer;

(C) a hydrolysis-stable, water-soluble monomer having one polymerizable double bond and optionally a carboxylic acid group, said monomer having a molecular weight of at most 200 Da, and said monomer is selected from the group consisting of 2-hydroxyethyl acrylamide, N,N-dimethyl(meth)acrylamide, N,N-diethyl (meth)acrylamide, N,N-di-n-propyl(meth)acrylamide, N-ethyl-N-methyl(meth)acrylamide and a compound represented by the formula (4)

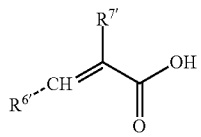

(4')

wherein $R^6$ is a hydrogen atom or a straight chain or branched $C_{1-3}$ alkyl group, and $R^7$ is a hydrogen atom or a straight-chain or branched $C_{1-6}$ alkyl group which may be substituted with a COOH group; and (D) a polymerization initiator system.

2. The aqueous dental glass ionomer composition according to claim 1, wherein the hydrolysis-stable, water-soluble monomer according to (C) is contained in an amount of from 5 to 30 percent by weight based on the total weight of the aqueous dental glass ionomer composition.

3. The aqueous dental glass ionomer composition according to claim 1, which further comprises (E) a polymerizable hydrolysis-stable crosslinker having at least two polymerizable carbon-carbon double bonds; and/or (F) a non-reactive filler.

4. The aqueous dental glass ionomer composition according to claim 1, wherein the molar ratio of first copolymerizable monomer to second copolymerizable monomer in the mixture copolymerized in step a) (mol first copolymerizable monomer/mol second copolymerizable monomer) is in the range of from 100:1 to 100:50.

5. The aqueous dental glass ionomer composition according to claim 1, wherein the coupling reaction in step b) is an addition reaction or a condensation reaction forming a bond selected from a group consisting of an amide bond, a urea bond and a thiourea bond.

6. The aqueous dental glass ionomer composition according claim 1, wherein the first copolymerizable monomer is represented by the general formula (1):

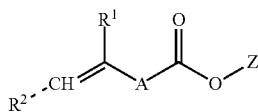

wherein
$R^1$ is a hydrogen atom, a —COOZ group or a straight chain or branched $C_{1-6}$ alkyl group which may be substituted by a —COOZ group;
$R^2$ is a hydrogen atom, a —COOZ group or a straight-chain or branched $C_{1-6}$ alkyl group which may be substituted by a —COOZ group;
A is a single bond or a straight-chain or branched $C_{1-6}$ alkylene group which group may contain 1 to 3 heteroatoms in between two carbon atoms of the alkylene carbon chain, which heteroatoms are selected from an oxygen atom, nitrogen atom, and sulfur atom, and/or which alkylene group may contain in between two carbon atoms of the alkylene carbon chain 1 to 3 groups selected from an amide bond or a urethane bond;
Z which may be the same or different, independently represents a hydrogen atom, a metal ion, a protecting group for a carboxylic acid group, or the Z forms with a further —COOZ group present in the molecule an intramolecular anhydride group.

7. The aqueous dental glass ionomer composition according claim 1, wherein the second copolymerizable monomer is represented by the general formula (2):

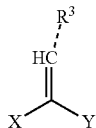

wherein
$R^3$ is a hydrogen atom or a straight chain or branched $C_{1-6}$ alkyl group which may be substituted by a —COOZ' group;
X is a protected amino group or a hydrocarbon group having 1 to 20 carbon atoms, which is substituted with an amino group which may carry a protecting group, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups;
Y is a hydrogen atom, a —COOZ' group, or a hydrocarbon group having 1 to 20 carbon atoms, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups;
Z' which may be the same or different, independently represents a hydrogen atom, a metal ion, a protecting group for a carboxylic acid group, or the Z' forms with a further —COOZ' group present in the molecule an intramolecular anhydride group.

8. The aqueous dental glass ionomer composition according to claim 1, wherein the compound having a polymerizable moiety and a functional group reactive with an amino group of repeating units derived from the second copolymerizable monomer is a compound represented by the general formula (3):

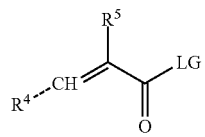

wherein
$R^4$ is a hydrogen atom or a straight chain or branched $C_{1-6}$ alkyl group which may be substituted by a —COOZ" group;
$R^5$ is a hydrogen atom or a straight-chain or branched $C_{1-6}$ alkyl group which may be substituted by a —COOZ" group;
Z" which may be same or different, independently represents a hydrogen atom, a metal ion, a protecting group for a carboxylic acid group, or the Z" forms with a further —COOZ" group present in the molecule an intramolecular anhydride group; and
LG is a leaving group, or wherein
LG may replace Z" and form with $R^4$ or $R^5$ an intramolecular carboxylic acid anhydride group, or wherein
two molecules of formula (3) form an intermolecular carboxylic acid anhydride group by condensation of LG and/or —COOZ", wherein LG is an oxygen atom.

9. The aqueous dental glass ionomer composition according claim 1, wherein the water-soluble monomer having one polymerizable double bond is itaconic acid or acrylic acid.

10. The aqueous dental glass ionomer composition according to claim 1, wherein the polymerizable polymer comprising acidic groups has a molecular weight $M_w$ in the range of from $10^3$ Da to $10^6$ Da.

11. The aqueous dental glass ionomer composition according to claim 1, wherein the particulate glass comprises
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

12. The aqueous dental glass ionomer composition according to claim 1, comprising 20 to 80 percent by weight of the reactive particulate glass, based on the total weight of the composition and/or comprising 10 to 80 percent by weight of the polymer comprising acidic groups, based on the total weight of the composition, and/or comprising up to 75 percent by weight of dispersed nanoparticles based on the total weight of the composition.

13. The aqueous dental glass ionomer composition according to claim 1, which, when cured, has at least one of the following mechanical characteristics:
an adhesive bond strength to dentin of at least 5 MPa as measured according to ISO 29022:2013; and/or
a flexural strength of at least 80 MPa as measured according to ISO 4049.

14. A dental composition comprising a mixture comprising
a water-soluble, polymerizable polymer comprising acidic groups, which is reactive with the particulate glass in a cement reaction, whereby the polymerizable polymer has a polymer backbone and hydrolysis-stable pendant groups having one or more polymerizable carbon-carbon double bonds, wherein the polymerizable polymer is obtainable by a process comprising
a) a step of copolymerizing a mixture comprising
   (i) a first copolymerizable monomer comprising at least one optionally protected carboxylic acid group and a first polymerizable organic moiety, and
   (ii) a second copolymerizable monomer comprising one or more optionally protected primary and/or secondary amino groups and a second polymerizable organic moiety,
   for obtaining an amino group containing copolymer;
b) a step of coupling to the amino group containing copolymer a compound having a polymerizable moiety and a functional group reactive with an amino group of repeating units derived from the second copolymerizable monomer in the amino group containing copolymer obtained in the first step, wherein the optionally protected amino group is deprotected, so that polymerizable pendant groups are linked to the backbone by hydrolysis-stable linking groups,
and, optionally, a step of deprotecting the protected carboxylic acid group after step a) or step b), for obtaining a polymerizable polymer;
and said mixture further comprises a hydrolysis-stable, water-soluble monomer having one polymerizable double bond and optionally a carboxylic acid group, said monomer having a molecular weight of at most 200 Da; and said monomer is selected from the group consisting of 2-hydroxyethyl acrylamide, N,N-dimethyl(meth)acrylamide, N,N diethyl(meth)acrylamide, N,N-di-n-propyl(meth)acrylamide, N-ethyl-N methyl (meth)acrylamide and a compound represented by the formula (4)

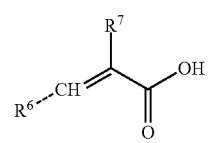

(4)

wherein
$R^6$ is a hydrogen atom or a straight-chain or branched $C_{1-3}$ alkyl group, and
$R^7$ is a hydrogen atom or a straight-chain or branched $C_{1-6}$ alkyl group which may be substituted with a —COOH group.

* * * * *